(12) United States Patent
Natarajan et al.

(10) Patent No.: US 10,175,174 B2
(45) Date of Patent: Jan. 8, 2019

(54) PHOTOACTIVATED CHEMICAL BLEACHING OF DYES

(71) Applicant: GE Healthcare Bio-Sciences Corp., Marlborough, MA (US)

(72) Inventors: Arunkumar Natarajan, Niskayuna, NY (US); Robert John Filkins, Niskayuna, NY (US); Anup Sood, Niskayuna, NY (US); Lakshmi Sireesha Kaanumalle, Niskayuna, NY (US); Kashan Ali Shaikh, Niskayuna, NY (US); Christina Lowes, Niskayuna, NY (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 623 days.

(21) Appl. No.: 14/648,176

(22) PCT Filed: Dec. 11, 2013

(86) PCT No.: PCT/US2013/074328
§ 371 (c)(1),
(2) Date: May 28, 2015

(87) PCT Pub. No.: WO2014/093455
PCT Pub. Date: Jun. 19, 2014

(65) Prior Publication Data
US 2015/0316482 A1 Nov. 5, 2015

Related U.S. Application Data

(60) Provisional application No. 61/735,586, filed on Dec. 11, 2012.

(51) Int. Cl.
*G01N 21/75* (2006.01)
*G01N 33/53* (2006.01)
*G01N 33/58* (2006.01)

(52) U.S. Cl.
CPC ......... *G01N 21/75* (2013.01); *G01N 33/5306* (2013.01); *G01N 33/582* (2013.01)

(58) Field of Classification Search
None
See application file for complete search history.

(56) References Cited

U.S. PATENT DOCUMENTS

| 5,169,473 A | 12/1992 | Bertram et al. |
| 5,661,035 A | 8/1997 | Tsien et al. |
| 6,630,356 B1 | 10/2003 | Armstrong et al. |
| 7,629,125 B2 | 12/2009 | Sood et al. |
| 7,741,046 B2* | 6/2010 | Larsen et al. ........ G01N 33/542 435/6.16 |
| 7,858,386 B2 | 12/2010 | Medintz et al. |
| 8,309,059 B2 | 11/2012 | Corona et al. |
| 8,568,991 B2* | 10/2013 | Natarajan et al. ..... G01N 21/64 435/7.1 |
| 2009/0088334 A1 | 4/2009 | Muraya et al. |

FOREIGN PATENT DOCUMENTS

| JP | H11-315117 A | 11/1999 |
| JP | 2002-365218 A | 12/2002 |
| WO | 2009/126380 A2 | 10/2009 |
| WO | 2013/095896 A1 | 6/2013 |

OTHER PUBLICATIONS

Edwards et al., "Modulation of Gap Junction-Dependent Arterial Relaxation by Ascorbic Acid," J. Vasc. Res., 2007, 14:410-422.
Japanese Office Action for JP Application No. 2015-545948 dated Sep. 26, 2017 (7 pages).
International Search Report and Written Opinion regarding International Application No. PCT/US2013/074328, dated Mar. 24, 2014, 12 pages.
Edwards DH et al., "Modulation of Gap Junction-Dependent Arterial Relaxation by Ascorbic Acid," Journal of Vascular Research, vol. 44, Jun. 20, 2007, pp. 410-422.

* cited by examiner

*Primary Examiner* — Kaijiang Zhang
(74) *Attorney, Agent, or Firm* — Eversheds Sutherland (US) LLP

(57) ABSTRACT

Methods comprising the use of photoactivated chemical bleaching for detecting multiple targets in a biological sample are provided. The methods include the steps of providing a biological sample including multiple targets, binding at least one probe to one or more target present in the sample, and detecting a signal from the probe. The method further includes the steps of contacting the sample comprising the bound probe with an electron transfer reagent, as well as an optional additive which prevents target modification during photoactivated chemical bleaching, and irradiating the sample, thereby initiating a photoreaction that substantially inactivates the probe by photoactivated chemical bleaching. The method further includes the steps of binding at least one probe to one or more target present in the sample, and detecting a signal from the probe. The process of binding, defecting and bleaching may be iteratively repeated.

41 Claims, 18 Drawing Sheets

FIG. 2
CYTOKERATIN AE1-Cy3
Cy3 CONJUGATE ON BREAST ADENOCARCINOMA
SIGNAL LOSS →
2 MIN PHOTOACTIVATED BLEACHING
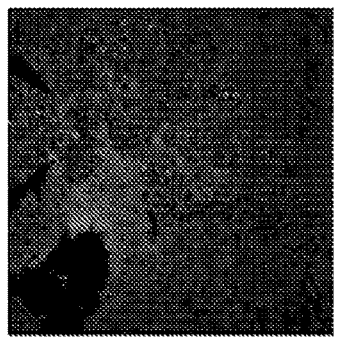
Cy3 CONJUGATE ON BLADDER CARCINOMA
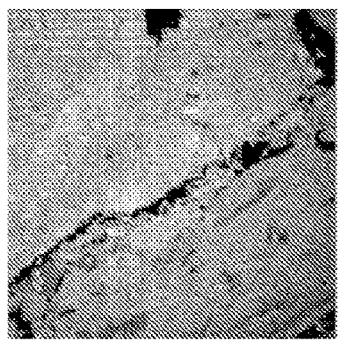
→
2 MIN PHOTOACTIVATED BLEACHING
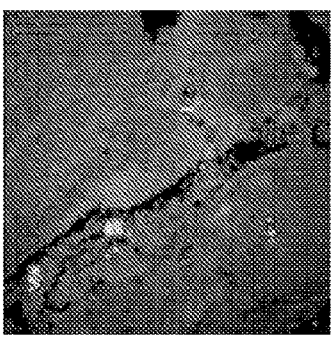

FIG. 3
PAN CADHERIN-Cy5
Cy5 CONJUGATE ON THYMUS
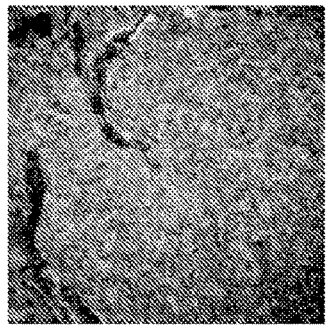
SIGNAL LOSS →
2 MIN PHOTOACTIVATED BLEACHING
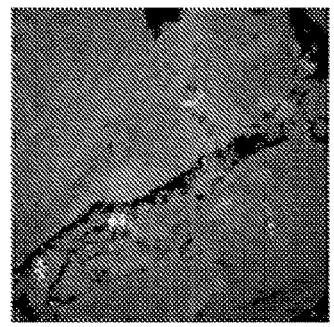
Cy5 CONJUGATE ON TONSIL
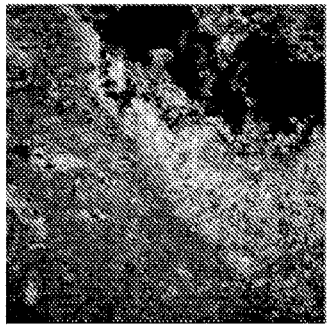
→
2 MIN PHOTOACTIVATED BLEACHING
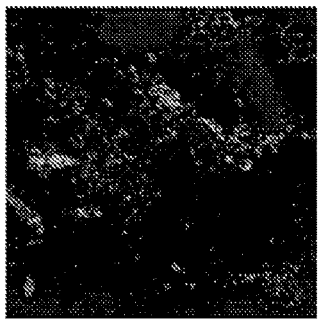

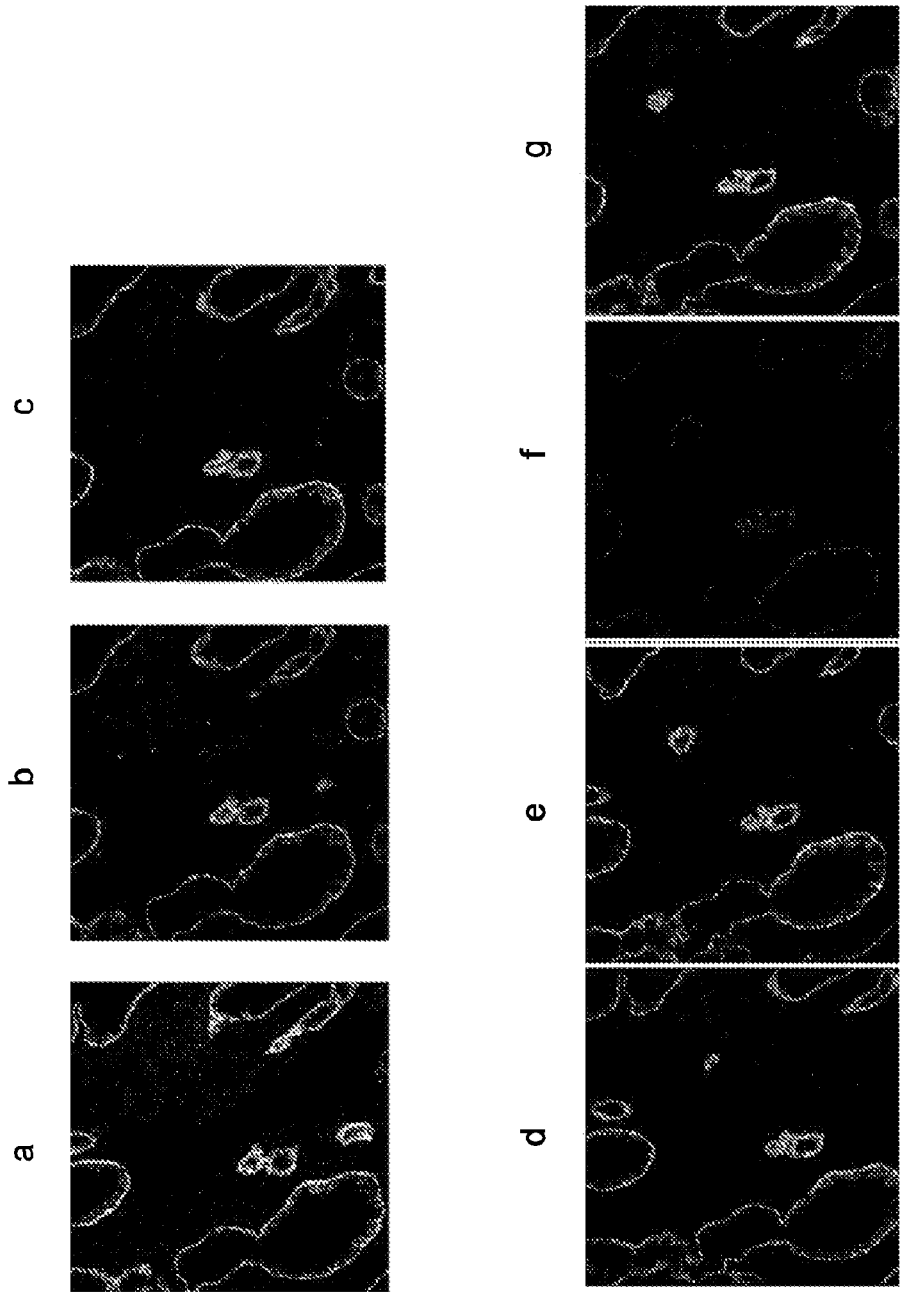

FIG. 14
a
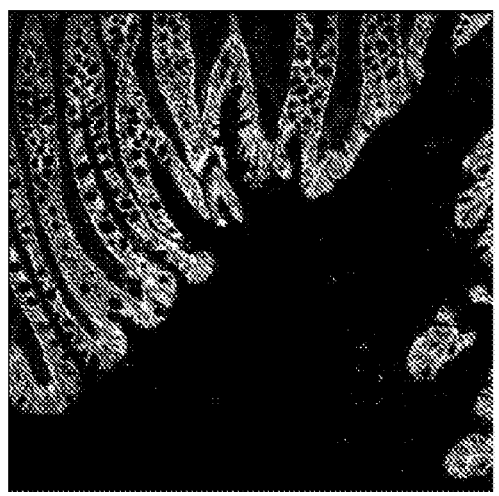
b
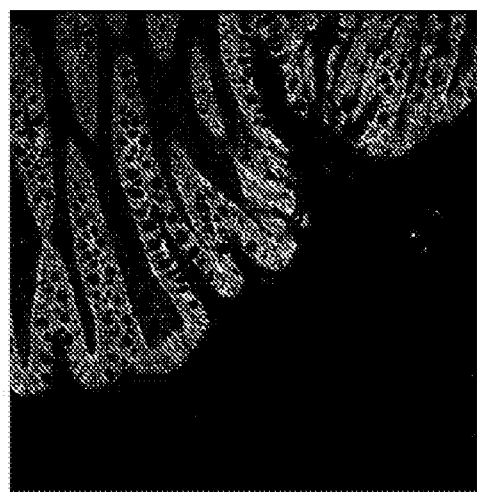
c
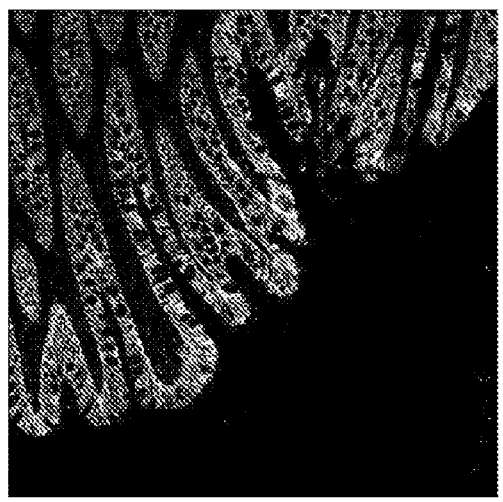
d
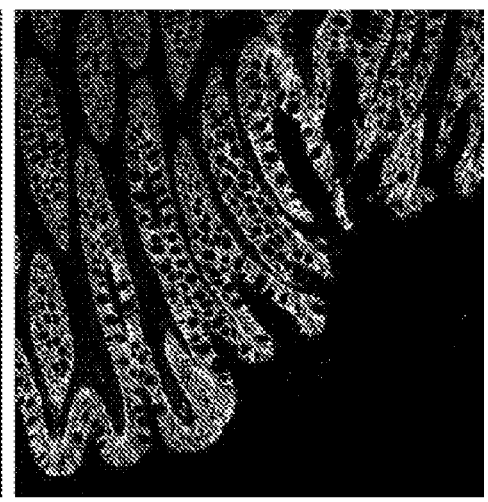

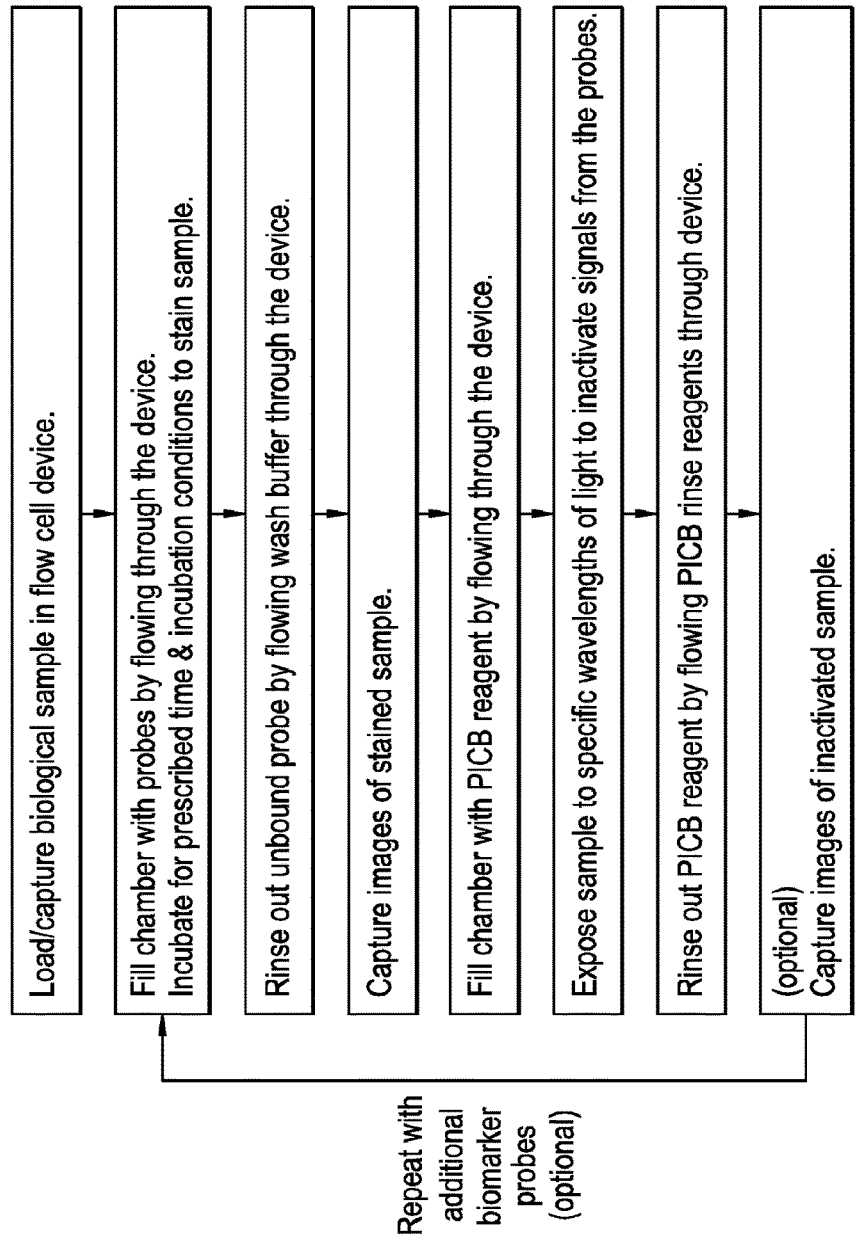

PHOTOACTIVATED CHEMICAL BLEACHING OF DYES

This application is a filing under 35 U.S.C. 371 of international application number PCT/US2013/074328, filed Dec. 11, 2013, which claims priority to U.S. application No. 61/735,586, filed Dec. 11, 2012, the entire disclosures of each of which are hereby incorporated by reference.

FIELD OF THE INVENTION

The present invention is directed to the detection of biomarkers on a biological sample. More specifically, the present invention is directed to the use of photoactivated chemical bleaching in a method for detecting multiple targets in a biological sample, including the optional use of an additive thus preventing target modification during photoactivated chemical bleaching process. Also provided are a kit and a system for performing the novel method, as well as images of a biological sample generated using the novel method.

BACKGROUND

Various methods may be used in biology and in medicine to detect different targets in a biological sample. For example, analysis of proteins in histological sections and other cytological preparations may be performed using the techniques of histochemistry, immunohistochemistry (IHC), or immunofluorescence. Analysis of proteins in biological samples may also be performed using solid-state immunoassays, for example, using the techniques of western blots, or using cell-based assays that can be performed, for example, by using flow cytometry.

Many of the current techniques may detect only a few targets at one time (such as IHC or fluoresence-based Western blots where number of targets detectable is limited by the fluorescence-based detection system) in a single sample. Further analysis of targets may require use of additional biological samples from the source, limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

Methods of iteratively analyzing an individual sample are described in U.S. Pat. No. 7,629,125 and U.S. Pat. No. 7,741,046. In particular, U.S. Pat. No. 7,741,046 provides methods of detecting multiple targets in a biological sample that involve the use of oxidation for inactivating signal generators (e.g., for bleaching fluorescent dyes.) The oxidation reaction is accomplished by using oxidizing reagents, such as hydrogen peroxide.

Additionally, a signal can be inactivated by continuous exposure of the signal generator to irradiation, i.e., by photobleaching. Similar to signal inactivation by oxidation, this process can be lengthy and may not proceed to completion, resulting in reduced signal-to-noise ratio. In addition, continued exposure of sample to irradiation may damage the biological sample.

However, these prior methods do occasionally affect protein epitopes and in such cases either these epitopes have to be detected in the first round or antibodies to alternate epitopes or downstream pathway proteins have to be used to study their effects on disease. In some cases the antigenicity is further enhanced for targets tested in later rounds preventing meaningful comparison of expression.

The concept of using scavengers to scavenge radicals, singlet oxygen is known. However, the concept has not been used for signal cycling on biological samples. Free radicals and singlet oxygen scavengers: Reaction of a peroxy-radical with β-carotene, diphenyl furan and 1,4-diazobicyclo(2,2,2)-octane, *Biochemical and Biophysical Research Communication*, Volume 98, Issue 4, 27 Feb. 1981, Pages 901-906. Oxygen Scavengers and Sensitizers for Reduced Oxygen Inhibition in Radical Photopolymerization Journal of Polymer Science Part A: Polymer Chemistry, Volume 46, Issue 20, 6916. Reduced Photobleaching of Conjugated Polymer Films through Small Molecule Additives, *Macromolecules* 2008, 41, 8306-8308.

Thus, there still remains a need for fast, milder and more sensitive methods for sequential analysis of biological targets.

BRIEF DESCRIPTION

Disclosed herein are novel methods for high-throughput multiplexing sample analysis. The methods employ, e.g., a signal cycling process wherein in each cycle, a photoreaction step allows the same signal generators, e.g., fluorophores, to be reused in the subsequent cycle to detect additional markers, e.g., proteins. These methods can be employed, e.g., for sequentially analyzing a biological sample to discern, among other things, the presence, absence, concentration, and/or spatial distribution of multiple biological targets in a biological sample. The photoreaction step can include applying an electron transfer agent, e.g., a borate salt, and initiating a photoreaction, e.g., by irradiating the sample with visible light, to inactivate the signal generator, e.g., fluorescent dye. The photoreaction step may further include an additive which prevents target modification caused by the photoreaction by-product, e.g., free radicals and singlet oxygen.

In some embodiments, advantages of the disclosed methods may include the rapid destruction of signal in each cycle. For example, in some instances, quenching is observed in about 100 milliseconds as compared to more than 15 minutes in conventional methods. In some embodiments, the disclosed methods also may be characterized by the absence of residual fluorescence even in high expression targets resulting, e.g., in increased signal-to-noise ratio. Also, the disclosed methods do not damage the biological sample or its components, e.g., the epitopes, such that the same sample may be used for many dozens of cycles. Also, in some embodiments, when compared to direct photobleaching of fluorescent dyes, the disclosed methods are advantageous because they do not require high power light which may damage biological sample components.

In some embodiments, the present invention is a method of probing multiple targets in a biological sample comprising:
  (a) binding at least one probe to one or more targets present in the biological sample including multiple targets;
  (b) detecting a signal from the at least one probe bound in step (a);
  (c) contacting the sample comprising the bound probe of step (a) with an electron transfer reagent and an additive which prevents target modification during step (d);
  (d) irradiating the sample of stop (c);
  (e) binding at least one probe to one or more targets present in the sample of step (d); and
  (f) detecting a signal from the probe bound in step (e).

In some embodiments, the probe in step (a) comprises an optical signal generator, and the signal detected in step (b) is an optical signal. In further embodiments, the optical signal generator is a fluorescent signal generates, and the optical signal detected in step (b) is a fluorescent signal.

In some embodiments, step (a) includes binding more than one probe to two or more targets.

In some embodiments, irradiating the sample in step (d) is carried out in the presence of a buffer. In some embodiments, irradiating is carried out at pH 5-9. In some embodiments, irradiating is carried out at pH 6-8.

In some embodiments, irradiating the sample in step (d) is carried out at the temperature of 4-50° C. In a preferred embodiment, irradiating the sample is carried out at the temperature of 20-30° C.

In some embodiments, irradiating the sample in step (d) is accomplished by exposing the sample to light of 350 nm-1.3 μM in wavelength. In some embodiments, irradiating the sample is accomplished by exposing the sample to light of 400-700 nm in wavelength.

In some embodiments, the electron transfer reagent is a borate salt. In some embodiments, the borate salt is represented by the following structural formula:

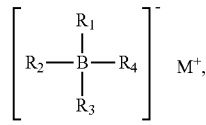

wherein:
  each $R_1$, $R_2$, and $R_3$ is, independently, an alkyl, an alkenyl, an akynyl, an aryl or a heteroaryl, wherein the alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro.
  $R_4$ is an alkyl, an alkenyl, or an akynyl, wherein the alkyl, alkenyl, or alkynyl is optionally substituted with one or more substituents selected from the group consisting of (C1-C4)alkyl, (C1-C4)alkoxy, (C1-C4)alkylamino, amino, hydroxyl, cyano, halogen, or nitro, and
  $M^+$ is selected from the group consisting of organic and inorganic cations.

In some embodiments, each $R_1$, $R_2$, and $R_3$ is aryl. In some embodiments, the aryl is phenyl. In some embodiments, the phenyl is an unsubstituted phenyl.

In some embodiments, $R_4$ is an optionally substituted alkyl. In some embodiments, $R^4$ unsubstituted butyl.

In some embodiments, each $R_1$, $R_2$, and $R_3$ is an optionally substituted aryl and $R_4$ is an optionally substituted alkyl. In a further embodiment, each $R_1$, $R_2$, and $R_3$ is unsubstituted phenyl and $R_4$ is unsubstituted butyl, and the borate salt is triphenylbutyl borate salt.

In some embodiments, the electron transfer reagent is a high water solubility borate salt. In some embodiments, the high water solubility borate salt is a pegylated borate salt. In other embodiments high water solubility borate salt is a tetraalkylborate.

In some embodiments, $M^+$ is an inorganic cation. In some embodiments, the inorganic cation is $Li^+$, $Na^+$ or $K^+$.

In some embodiments, the probe comprises a binder and a signal generator. In some embodiments, the signal generator is a fluorescent signal generator. In some embodiments, the fluorescent signal generator comprises a cyanine dye. In some embodiments, the cyanine dye is Cy3 or Cy5.

In some embodiments, the cyanine dye is Cy3; irradiation of the sample in step (e) is accomplished by using optical filters, comprises exposing the sample to light of 520-580 nm in wavelength; and results in selective photoexcitation of Cy3.

In some embodiments, the cyanine dye is Cy5; irradiation of the sample in step (e) is accomplished by using optical fibers; comprises exposing the sample to light of 620-680 nm in wavelength; and results in selective photoexcitation of Cy5.

In some embodiments, the biological sample in step (a) comprises cell organelles, whole cells or tissue sections. In some embodiments, the sample comprises proteins, carbohydrates or nucleic acids.

In some embodiments, steps (c)-(f) are repeated one or more times. In some embodiments, steps (c)-(f) are repeated at least 5, at least 15, at least 30, at least 60, at least 100 or at least 150 times. In some embodiments, steps (c)-(f) are repeated 25-30 times. In other embodiments, steps (c)-(f) are repeated 2-10 times.

In some embodiments, steps (c) and (d) are performed for about 1 millisecond to about 60 minutes. In some embodiments, steps (c) and (d) are performed for about 100 milliseconds to about 15 minutes. In some embodiments, the steps (c) and (d) are performed for about 1 second to about 5 minutes.

In some embodiments, steps (c) and (d) are performed at a temperature of 4-50° C. In a preferred embodiment, the steps (c) and (d) are performed at a temperature of 20-30° C.

In some embodiments, the method also comprises measuring one or more intensity values of the signal detected in detecting step (b), step (f), or steps (b) and (f). In some embodiments, the method further comprises correlating the intensity value with an amount of target present in the sample.

In some embodiments, the probe in step (a) and the probe in step (e) each comprise a signal generator. In some embodiments, the signal generator in step (a) is the same as the signal generator in step (e). In other embodiments, the signal generator in step (a) is different from the signal generator in step (e).

In some embodiments, the signals detected in step (b) and step (f) are both detectable in a single detection channel. In other embodiments, the signal detected in step (b) or step (f) is independently detectable in different detection channels.

In some-embodiments, the components of the biological sample that are different from the probe are not significantly modified.

In some embodiments, no detectable signal is detected after step (d).

In some embodiments, the signal generator comprises a chromophore, or a Raman-active tag.

In some embodiments, the additive which prevents target modification is a free radical scavenger. In a preferred embodiment, the free radical scavenger is selected from the group consisting of ascorbic acid, n-propyl gallate, mercaptoethanol, cysteine hydrochloride, t-butyl hydroxy toluene, cycloheptatriene, dioctyl phthalate, 1,4-Dihydro-o-toluamide, a-tocopherol and trolox.

In other embodiments, the additive which prevents target modification is a quencher for singlet oxygen. In a preferred embodiment, the quencher for singlet oxygen is selected from the group consisting of ascorbic acid, a-tocopherol, curcumin and DABCO.

In some embodiments, the method of probing multiple targets in a biological sample further comprises, after step (d), washing the sample with a wash solution that effectively removes residual electron transfer reagents from the sample. In some embodiments one or more enablers may be added to the wash solution that may facilitate removal of residual electron transfer reagent by increasing it solubility in the wash solution. In some embodiments these enablers include organic solvent, cationic reagents, chaotropes, detergents or a combination thereof. In preferred embodiments the enabler is ethanol. In the most preferred embodiment the enabler is 70% ethanol.

In some embodiments, the present invention is a method of probing multiple targets in a biological sample comprising:
(a) binding multiple probes to multiple targets present in the biological sample including multiple targets;
(b) detecting a first set of signals from the first set of probes bound in step (a);
(c) contacting the sample comprising the bound probes of step (a) with as electron transfer reagent and an additive which prevents target modification in step (d);
(d) irradiating the sample of step (c);
(e) generating a second set of signals from the second set of probes bound in step (a);
(f) detecting the second set of signals.

In some embodiments, irradiation of sample in step (d) initiates a photoreaction that substantially inactivates the signal generator by photoactivated chemical bleaching. In some embodiments, the photoreaction comprises intermolecular electron transfer. In other embodiments, the photoreaction comprises intramolecular electron transfer.

In some embodiments, the signal generator is irreversibly modified. In some embodiments, the signal generator is irreversibly modified by a photoreaction that inactivates the signal generator by photoactivated chemical bleaching.

In some embodiments, the method of probing multiple targets in a biological sample further comprises, after step (d), washing the sample with a wash solution that effectively removes residual electron transfer reagents from the sample. In some embodiments, the wash solution contains ethanol.

In some embodiments, the present invention is a high throughput multiplexing biological sample analysis method, the method comprising:
a signal cycling process, wherein in each cycle, staining and imaging is followed by applying an electron transfer reagent and an additive which prevents target modification and irradiation of the biological sample.

In some embodiments, the high throughput multiplexing biological sample analysis method comprises, in each cycle, washing the sample with a wash solution that effectively removes residual electron transfer reagents from the sample. In some embodiments, the wash solution contains ethanol.

In some embodiments, the method allows rapid signal cycling without significantly modifying the components of the biological sample that are different from the probe.

In some embodiments, the present invention is a kit for bleaching a signal for probing multiple targets in a biological sample, comprising:
an electron transfer reagent that, when contacted with a signal generator, is capable of bleaching the signal generator upon irradiation; and
an additive which prevents target modification during photoactivated chemical bleaching of the signal generator.

In certain embodiments, the kit for bleaching a signal may further include additional components for probing multiple targets in a biological sample. For example, the kit may include an antigen retrieval solution. The kit may also include a solution that blocks non-specific binding of a probe to the biological sample. In other embodiments, kit may also include an enabler, a reagent when added to wash solution helps removal of residual borate after signal removal.

In some embodiments, the present invention is a method for using the kit to bleach a signal for the purpose of enabling a signal cycling process for probing multiple targets in a biological sample, comprising: after detecting a signal from at least one probe bound to one or more targets present in a biological sample, contacting the sample with the electron transfer reagent and the additive which prevents target modification; and irradiating the sample.

In some embodiments, the present invention is a kit for probing multiple targets in a biological sample comprising:
multiple probes comprising a binder coupled to a signal generator;
an electron transfer reagent that, when contacted with the signal generator, is capable of bleaching the signal generator upon irradiation; and
an additive which prevents target modification during photoactivated chemical bleaching of the signal generator.

In certain embodiments, the kits further include an instruction for using the kit.

In some embodiments, the present invention is a series of at least two images depicting optically labeled biological targets wherein:
the images are obtained in the process of probing multiple targets in a biological sample, wherein the process comprises:
(a) binding at least one optical probe to one or more targets present in the biological sample including multiple targets;
(b) detecting a signal from the optical probe bound in step (a);
(c) contacting the sample comprising the bound optical probe of step (a) with an electron transfer reagent and an additive which prevents target modification in step (d);
(d) irradiating the sample of step (c);
(e) binding at least one optical probe to one or more targets present in the sample of step (d); and
(f) detecting a signal from the optical probe bound in step (e).

In some embodiments, the present invention is a method of probing targets in a biological sample comprising:
(a) as binding at least one probe to one or more targets present in the biological sample including multiple targets:
(b) detecting a signal from the probe bound in step (a);
(c) contacting the sample comprising the bound probe of step (a) with an electron transfer reagent and an additive which prevents target modification in step (d); and
(d) irradiating the sample of step (c).

In some embodiments, the present invention is a method of probing multiple targets in a biological sample comprising:
(a) binding at least one probe to one or more targets present in the biological sample including multiple targets:
(b) binding at least one control probe to one or more targets present in the sample;
(c) detecting a signal from the probe bound in step (a) and a control signal from the control probe bound in step (b);

(d) contacting the sample in step (c) with an electron transfer reagent that is capable of selectively reacting with the probe and not the control probe and an additive which prevents target modification in step (e);

(e) irradiating the sample of step (d);

(f) binding at least one probe to one or more targets present in the sample of step (e); and (g) detecting a signal from the probe bound in step (f).

In some embodiments, the steps (a) and (b) are performed simultaneously. In some embodiments, the step (g) also comprises detecting a signal from the control probe bound in step (b).

In some embodiments, the method of probing multiple targets in a biological sample further comprises, after step (e), washing the sample with a wash solution that effectively removes residual electron transfer reagents from the sample. In some embodiments, the wash solution contains ethanol.

In some embodiments, the present invention is an automated process for photoactivated chemical bleaching of a biological sample loaded/captured in a flow cell device, comprising the following automated steps of a) binding at least one probe to one or more targets present in the biological sample;

b) detecting a signal from the at least one probe bound in step (a);

c) filling the flow cell with an electron transfer reagent and optionally an additive which prevents target modification during subsequent sample irradiation:

d) irradiating the sample by exposure to light to inactivate signals from the probe; and e) repeating steps a) and b) with at least one other probe, for another round of imaging.

In certain embodiments, after sample irradiation, the automated process also includes an optional wash step to wash out the electron transfer reagent and the additive. In other embodiments, the electron transfer reagent and the additive may be washed out during the subsequent probe binding step a). In other embodiments, the electron transfer reagent and the additive may be washed out during an optional step that removed excess probe before subsequent signal detection step b). These latter embodiments are particularly suited for high solubility borate electron transfer reagents.

In certain embodiments of the automated process for photoactivated chemical bleaching, sample irradiation is accomplished by exposing specific regions of the sample to light using optical filters, a microscope objective, and a translation stage. In other embodiments, sample irradiation is accomplished by exposing the entire sample at once to light.

DESCRIPTION OF THE FIGURES

FIG. 2 shows grayscale images of samples stained with Cy3-conjugated cytokeratin before and after photoactivated chemical bleaching.

FIG. 3 shows grayscale images of samples stained with Cy5-conjugated pan cadherin before and after photoactivated chemical bleaching.

FIG. 11(a) Evaluation of different reagents/buffers for removing residual borate as measured by subsequent effects on signal from next round of staining and prolonged light exposure.

FIG. 14: Elimination of extra washing steps by use of a higher water solubility (tetrabutylborate) borate. a & b) samples bleached with monobenzyl triphenylborate and washed with 70% ethanol (3×1 min) and PBS (3×5 min): c & d) samples bleached with tetrabutylborate and washed with PBS (3×5 min) alone.

FIG. 15: a flow chart for example steps of an automated process for photoactivated chemical bleaching for multiplexed analysis of a biological sample.

DETAILED DESCRIPTION

Definitions

Figure 1:
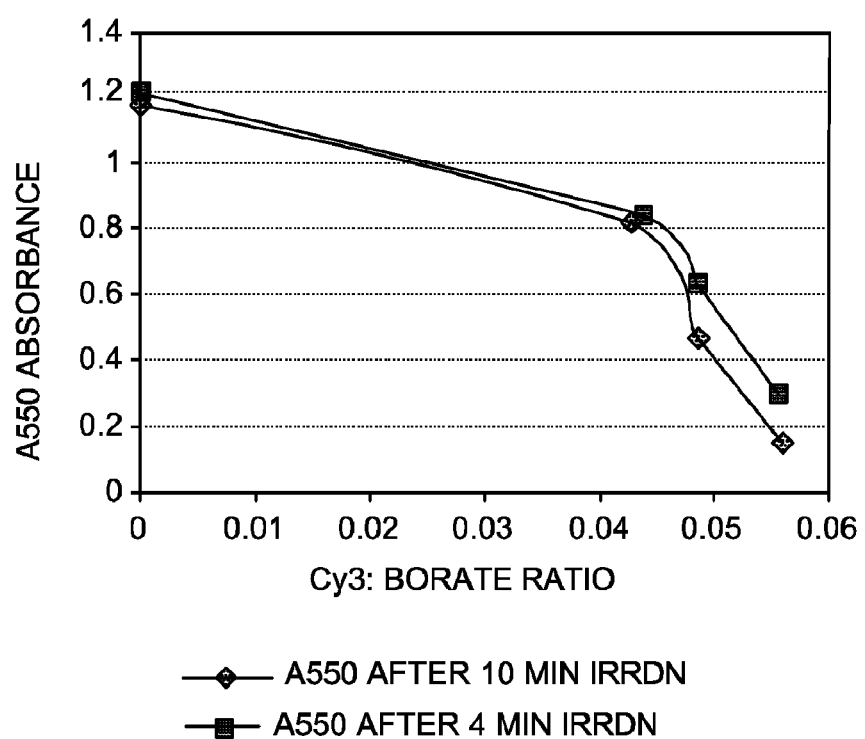
FIG. 1 is a grayscale image of a graph showing absorbance of Cy3 dye at 550 nm after incubation with different concentrations of triphenylbutyl borate lithium salt and irradiation for 4 or 10 minutes.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "additive" or "additive which prevents target modification" refers to either free radical scavengers or singlet oxygen quenchers. Free radical scavengers reform to any additives that react directly with a variety of radicals, including the peroxy radical (ROO.), CCl$_3$., and HO. as well as the superoxide radical (O$_2$.'). Examples of such additives are but not limited to, ascorbic add, n-propyl gallate, mercaptoethanol, cysteine hydrochloride, t-butyl hydroxy toluene (BHT), Cycloheptatriene (CHT), dioctyl phthalate (DOP), 1,4-Dihydro-toluamide (TA), a-tocopherol and trolox. Singlet oxygen quenchers include, for example, curcurmin and DABCO. Some free radical scavengers, such as a-tocopherol and ascorbic acid can also act as singlet oxygen scavenger.

As used herein, the term "alkyl" refers to saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.). In certain embodiments, a straight chain or branched chain alkyl has 6 or fewer carbon atoms in its backbone (e.g., $C_1$-$C_6$ for straight chain, $C_3$-$C_6$ for branched chain) or 4 or fewer carbon atoms in its backbone (e.g., $C_1$-$C_4$ for straight chain, $C_3$-$C_4$ for branched chain). The term "$C_1$-$C_6$" alkyl refers to alkyl groups containing 1 to 6 carbon atoms. The term "$C_1$-$C_4$" alkyl refers to alkyl groups containing 1 to 4 carbon atoms. Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, (C1-C4)alkyl, (C1-C4)alkoxy, amino (including (C1-C4) alkylamino and (C1-C4)dialkylamino), hydroxyl, cyano, halogen, or nitro. Cycloalkyls can be further substituted, e.g., with the substituents described above.

As used herein, the term "alkenyl" refers to unsaturated aliphatic groups analogous in length and possible substitution to the alky is described above, but that contain at least one double bond. For example, the term "alkenyl" includes straight-chain alkenyl groups (e.g., ethylenyl propenyl, butenyl, pentenyl, hexenyl, heptenyl, octenyl, nonenyl, decenyl, etc.), branched-chain alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, (C1-C4)alkyl, (C1-C4) alkoxy, amino (including (C1-C4)alkylamino and (C1-C4) dialkylamino), hydroxyl, cyano, halogen, or nitro.

As used herein, the term, "alkynyl" refers to unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), or branched-chain alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, (C1-C4)alkyl, (C1-C4) alkoxy, amino (including (C1-C4)alkylamino and (C1-C4) dialkylamino), hydroxyl, cyano, halogen, or nitro.

As used herein, the term "alkoxy" refers to substituted and unsubstituted alkyl, alkenyl, and alkynyl groups covalently linked to an oxygen atom. Examples of alkoxy groups include, but are not limited to, methoxy, ethoxy, isopropyloxy, propoxy, butoxy, and pentoxy groups. In certain embodiments, a straight chain or branched chain alkoxy has 4 or fewer carbon atoms in its backbone (e.g., $C_1$-$C_4$ for straight chain, $C_3$-$C_4$ for branched chain). The term "$C_1$-$C_4$" alkyl refers to alkyl groups containing 1 to 4 carbon atoms.

As used herein, the term "amine" or "amino" refers to compounds or substituents where a nitrogen atom is covalently bonded to at least one carbon or hereroatom. The term includes "alkyl amino" which comprises groups and compounds wherein: the nitrogen is bound to at least one additional alkyl group. The term "dialkyl amino" includes groups wherein; the nitrogen atom is bound to at least two additional alkyl groups. In certain embodiments, these alkyl groups have 4 or fewer carbon atoms in their backbone (e.g., $C_1$-$C_4$ for straight chain, $C_3$-$C_4$ for branched chain). The term (C1-C4)alkylamino refers to groups and compounds, wherein the nitrogen is bound to at least one additional C1-C4 alkyl group. The term "(C1-C4)dialkylamino refers to groups and compounds, wherein the nitrogen is bound to at least two additional C1-C4 alkyl groups.

As used herein, the term "aryl" refers to groups, e.g., 5- and 6-membered single-ring, aromatic groups, that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, (C1-C4)alkyl, (C1-C4)alkoxy, amino (including (C1-C4)alkylamino and (C1-C4)dialkylamino), hydroxyl, cyano, halogen, or nitro. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

As used herein, the term "antibody" refers to an immunoglobin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab').sub.2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractious, cells isolated from mammals including, humans and cell organelles. Biological samples also may include sections of the biological sample including tissues (e.g., sectional portions of an organ or tissue). Biological samples may also include extracts from a biological sample, for example, an antigen or a nucleic acid from a biological fluid (e.g., blood or urine). Biological samples may comprise proteins, carbohydrates or nucleic acids.

A biological sample may be of prokaryotic origin, archaeal origin, or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "control probe" refers to an agent having a binder coupled to a signal generator or a signal generator capable of staining directly, such that the signal generator retains at least 80 percent signal after contact with an electron transfer reagent and subsequent irradiation. A suitable signal generator in a control probe is not substantially inactivated, e.g., substantially bleached by photoactivated chemical bleaching, when contacted with the electron transfer reagent and irradiated. Suitable examples of signal generators may include a fluorophore that does not undergo bleaching under the conditions employed (e.g., DAPI).

As used herein the term "enabler" refers to a material added to the wash solution that helps in removal of residual electron transfer reagents from the sample after signal has been removed. A suitable enabler is one that increases the solubility of the electron transfer reagent in an aqueous buffer. The enabler may function by complexing with the electron transfer reagent, e.g. cationic salts when the electron transfer reagent is an anionic salt, disrupting non-covalent interactions and aggregation, e.g. chaotropes and detergents or modulate the hydrophilicity of the wash to make amphiphilic electron transfer reagents more soluble. Examples of suitable enablers include water soluble mono- or poly-cations, chaotropes, detergents and organic solvents.

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample. A receptor may be exogeneous (that is, a receptor extrinsically adhered to the sample or the solid-support) or endogeneous (receptors present intrinsically in the sample or the solid-support). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample. In some embodiments, enzyme substrates employed in the methods herein may include non-chromogenic or non-chemiluminescent substrates. A signal generator may be attached to the enzyme substrate as a label.

As used herein, the term, "electron transfer reagent" refers to a reagent that can engage in a photoreaction with a molecule capable of undergoing photoexcitation. This term also refers to a composition comprising a reagent that can engage in a photoreaction with a molecule capable of undergoing photoexcitation. In some embodiments, the molecule capable of undergoing photoexcitation may be a signal generator. In some embodiment, the electron transfer reagent may donate an electron to the signal generator in the course of a photoreaction. In alternative embodiments, the electron transfer reagent may accept an electron from the signal generator in the course of a photoreaction.

In some embodiments, the electron transfer reagent donating an electron to the signal generator in the course of a photoreaction may be a borate salt. In a further embodiment the borate salt is triphenylbutyl borate.

In alternative embodiments, the electron transfer reagent accepting an electron from the photoexcited molecule may be an onium salt [e.g., diphenyliodonium hexafluorophosphate (DPI) or dimethylphenacylsulfonium tetrafluoroborate (DMPS)], or tetrabutylammonium butyltriphenylborate (TBAB).

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin,-,4,4'-diisothiocyanatodihydro-stilbene-2,2'-disulfonic acid, 4,4'-diisothiocyanatostilbene-2,2'-disulfonic acid 5-[dimethylamino]naphthalene-1-sulfonyl chloride (DNS, dansyl chloride), fluorescein and derivatives such as 5-carboxyfluorescein (FAM), 5-(4,6-dichlorotriazin-2-yl) aminofluorescein (DTAF), 2'7'-dimethyoxy-4'5'dichloro-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; ophthaldialdehyde derivative (fluorescent upon reaction with amines); pyrene and derivatives such as pyrene, pyrene butyrate and succinimidyil 1-pyrene butyrate; Reactive Red 4 (Cibacron™ Brilliant Red 3B-A), rhodamine and derivatives such as 6-carboxy-X-rhodamine (ROX), 6-carboxyrhodamine (R6G) lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, cyanines, pyrelium dyes, squaraines, 1,3-dichloro-7-hydroxy-9,9-dimethyl-2(9H)-Acridinone (DDAO), and dimethylacridinone (DAO). In some embodiments, the fluorophore can be cyanine, rhodamine, BODIPY or 1,3-dichloro-7-hydroxy-9,9-dimethyl-2 (9H)-Acridinone (DDAO) dyes. In a preferred embodiment, the fluorophore is a cyanine dye. In a further embodiment, the cyanine dye is Cy3 or Cy5.

As used herein, the term "in situ" generally refers to an event occurring in the original location, tor example, in intact organ or tissue or in a representative segment of an organ or tissue. In some embodiment, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the terms "irradiation" or "irradiate" refer to act or process of exposing a sample or a solution to non-ionizing radiation. In some embodiments, the non-ionizing irradiation has wavelengths between 350 nm and 1.3 µm. In preferred embodiments, the non-ionizing radiation is visible light of 400-700 nm in wavelength. Irradiation may be accomplished by exposing a sample or a solution to a radiation source, e.g., a lamp, capable of emitting radiation of a certain wavelength or a range of wavelengths. In some embodiments, a molecule capable of undergoing photoexcitation is photoexcited as a result of irradiation. In some embodiments, the molecule capable of undergoing photoexcitation is a signal generator, e.g., a fluorescent signal generator. In some embodiments, irradiation of a fluorescent signal generator initiates a photoreaction between the fluorescent signal generator and the electron transfer reagent. In some embodiments, irradiation initiates a photoreaction substantially inactivates the signal generator by photoactivated chemical bleaching.

Optical filters may be used to restrict irradiation of a sample or a solution to a particular wavelength or a range of wavelengths. In some embodiments, the optical filters may be used to restrict irradiation to a narrow range of wavelengths for selective photoexcitation of one or more molecules capable of undergoing photoexcitation. The term "selective photoexcitation" refers to an act or a process, whereby one or more molecules capable of undergoing photoexcitation are photoexcited in the presence of one or more other molecules capable of undergoing photoexcitation that remain in the ground electronic state after irradiation.

In some embodiments, the molecule capable of undergoing photoexcitation is a fluorescent dye, e.g., a cyanine dye. In one further embodiment, irradiation limited to a range of wavelengths between 520-580 nm is used for selective photoexcitation of a Cy3 dye. In another further embodiment, irradiation limited to a range of wavelengths between 620-680 nm is used for selective photoexcitation of a Cy5 dye. In alternative embodiments, irradiation of a sample at a specific wavelength may also be accomplished by using a laser.

As used herein, the term "peroxidase" refers to an enzyme class that catalyzes an oxidation reaction of an enzyme substrate along with an electron donor. Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically catalyzed by peroxidase to form a reaction product. In some embodiments, peroxidase substrates employed in the methods herein may include non-chromogenic or non-chemiluminescent substrates. A fluorescent signal generator may be attached to the peroxidase substrate as a label.

As used herein, the term "bleaching", "photoactivated chemical bleaching" or "photoinduced chemical bleaching" refers to an act or a process whereby a signal generated by a signal generator is modified in the course of a photoreaction. In certain embodiments, the signal generator is irreversibly modified.

In some embodiments, the signal is diminished or eliminated as a result of photoactivated chemical bleaching. In some embodiments, the signal generator is completely bleached, i.e., the signal intensity decreases by about 100%. In some embodiments, the signal is an optical signal, and the signal generator is an optical signal generator. The term "photoactivated chemical bleaching" is meant to exclude photobleaching, or loss of signal (e.g., fluorescent signal) that may occur in the absence of electron transfer reagent, e.g., after continued irradiation of a signal generator, such as a fluorophore, or after its continued exposure to light.

As used herein, the term "photoexcitation" refers to an act or a process whereby a molecule transitions from a ground electronic state to an excited electronic state upon absorption of radiation energy, e.g. upon irradiation. Photoexcited molecules can participate in chemical reactions, e.g., in electron transfer reactions. In some embodiments, a molecule capable of undergoing photoexcitation is a signal generator, e.g., a fluorescent signal generator.

As used herein, the term "photoreaction" or a "photoinduced reaction" refers to a chemical reaction that is initiated and/or proceeds as a result of photoexcitation of at least one reactant. The reactants in a photoreaction may be an electron transfer reagent and a molecule capable of undergoing photoexcitation. In some embodiments, a photoreaction may involve an electron transfer from the electron transfer reagent to the molecule that has undergone photoexcitation, i.e., the photoexcited molecule. In alternative embodiments, a photoreaction may also involve an electron transfer from the molecule that has undergone photoexcitation to the electron transfer reagent. In some embodiments, the molecule capable of undergoing photoexcitation is a fluorescent signal generator, e.g., a fluorophore. In some embodiments, photoreaction results in irreversible modification of one or more components of the photoreaction. In some embodiments, photoreaction substantially inactivates the signal generator by photoactivated chemical bleaching.

In some embodiments, the photoreaction may involve an intermolecular electron transfer between the electron transfer reagent and the photoexcited molecule, e.g., the electron transfer occurs when the linkage between the electron transfer reagent and the photoexcited molecule is transitory, forming just prior to the electron transfer and disconnecting after electron transfer.

In some embodiments, the photoreaction may involve intramolecular electron transfer between the electron transfer reagent and the photoexcited molecule, e.g., the electron transfer occurs when the electron transfer reagent and the photoexcited molecule have been linked together, e.g., by covalent or electrostatic interactions, prior to initiation of the electron transfer process. The photoreaction involving the intramolecular electron transfer can occur, e.g., when the molecule capable of undergoing photoexcitation and the electron transfer reagent carry opposite charges and form a complex held by electrostatic interactions. For example, a cationic dye, e.g., a cationic cyanine dye and triphenylbutyl borate anion may form a complex, wherein intramolecular electron transfer may occur between the cyanine and borate moieties upon irradiation.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator. In some embodiments, the probe may comprise an optical signal generator, such that the signal observed is an optical signal. In some embodiments, the probe may comprise a fluorescent signal generator, such that the signal observed is a fluorescent signal.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal. Examples of signal generators include one or more of a chromophore, a flourophore, or a Raman-active tag. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

In some embodiments, the signal generator may be an optical signal generator. In some embodiments, the optical signal generator may be a fluorescent signal generator, e.g., a fluorophore. In preferred embodiments, the fluorescent signal generator may be a cyanine dye, e.g., Cy3, Cy5 or Cy7. In some embodiments, the signal generator, e.g., a fluorophore, may be charged. In one embodiment, the signal generator is a cationic fluorescent dye.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant ($K_A$) for the target no lower than about $10^5$ $M^{-1}$ under ambient conditions such as a pH of about 6 to about 8 and temperature ranging from about 0° C. to about 37° C.

As used herein, the term "target" refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

As used herein the term "target modification" includes a change in the target structure that prevents or reduces probe binding. The change may be chemical in nature, e.g. oxidation of or free radical addition to one or more amino acids, one or more lipid components, one or more nucleic acid bases or other components of samples that are being targeted for detection, or physical, such as denaturation of the protein or a portion of the protein, unwinding of DNA, increase in folding, etc.

The invention includes embodiments that relate generally to methods applicable in analytical, diagnostic, or prognostic applications such as analyte detection, fluorescence-activated cell sorting (FACS), histochemistry, immunohistochemistry, or immunofluorescence. In some embodiments, the methods disclosed herein may be particularly applicable in histochemistry, immunostaining, immunohistochemistry, immunoassays, or immunofluorescence. In some embodiments, the methods disclosed herein may be particularly applicable in immunoblotting techniques, for example, western blots or immunoassays such as enzyme-linked immunosorbent assays (ELISA).

The disclosed methods relate generally to detection of multiple targets in a single biological sample. In some embodiments, methods of detecting multiple targets in a single biological sample using the same detection channel are disclosed. The targets may be present on the surface of cells in suspension, on the surface of cytology smears, on the surface of histological sections, on the surface of DNA microarrays, on the surface of protein microarrays, or on the surface of solid supports (such as gels, blots, glass slides, beads, or ELISA plates).

The methods disclosed herein may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support (e.g., blots) without substantially stripping the probes and the targets. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about five as only about five fluorescent signals may be resolvable based on their excitation and emission wavelength properties. In some embodiments, the methods disclosed herein may allow detection of greater than five targets using fluorescent-based detection system.

In some embodiments, the method is a high throughput multiplexing biological sample analysis that includes a signal cycling process, wherein in each cycle, staining and imaging is followed by applying an electron transfer reagent, as well as an optional additive which prevents target modification, and irradiation of the biological sample. The method allows rapid signal cycling without significantly modifying the components of the biological sample that are different from the probe.

In some embodiments, the method of detecting multiple targets in a biological sample includes sequential detection of targets in the biological sample. The method generally includes the steps of detecting a first set of targets in the biological sample, bleaching the signal from the first set of targets by photoinduced chemical bleaching in the optional presence of an additive which prevents target modification. In some embodiments, the method includes a step of washing the sample with a wash solution that effectively removes residual electron transfer reagents from the sample. In some embodiments, the wash solution contains ethanol.

In some embodiments, the method further includes detecting a second set of targets in the biological sample. The method may further include repeating the step of photoinduced chemical bleaching of signal from the second set of targets, followed by detecting a third set of targets in the biological sample, and so forth.

In some embodiments, the method includes the steps of contacting a biological sample with a first probe and physically binding a first probe to a first target. The method further includes detecting/observing a first signal from the first probe. An electron transfer reagent and an optional additive which prevents target modification are applied to the probe, and the sample including the electron transfer reagent, the additive and the probe is irradiated, thereby initiating a photoreaction that modifies the first signal. The method further includes contacting the biological sample with a second probe and physically binding the second probe to a second target in the biological sample followed by detecting/observing a second signal from the second probe. In some embodiments, the method includes a step of washing the sample with a wash solution that effectively removes residual electron transfer reagents from the sample. In some embodiments, the wash solution contains ethanol.

In some embodiments, the method also includes the steps of contacting a biological sample with a plurality of multiple sets of probes and physically binding the plurality of probes to a plurality of targets. The method further includes detecting a first set of signals from the first set of the plurality of probes. An electron transfer reagent and an optional additive which prevents target modification are applied to the plurality of probes, and the sample is irradiated, thereby initiating a photoreaction that modifies the first set of signals from the first set of the plurality of probes. The method further includes generating the second set of signals from the second set of the plurality of targets and detecting the second set of signals. Generation of the second set of signals may comprise associating the second set of probes with a separate moiety that comprises signal generator. For example, the second set of probes may comprise a biotin tag, and the moiety comprising signal generator may also comprise streptavidin capable of binding the biotin tag. Alternatively, generation of the second set of signals may comprise unmasking the signal-generating moiety, e.g., by modifying the distance between the fluorophore-quencher pair. In yet another embodiment, the second set of signals may arise from hybridization of labeled nucleic acid probes to unlabeled complementary sequences on the second set of probes. In some embodiments, the method includes a step of washing the sample with a wash solution that effectively removes residual electron transfer reagents from the sample. In some embodiments, the wash solution contains ethanol.

It other embodiments, the method includes the steps of providing a sample including multiple targets and binding at least one probe having a binder coupled to an enzyme to one or more target present in the sample. The method further includes reacting the bound probe with an enzyme substrate coupled to a signal generator and observing a signal from the signal generator. An electron transfer reagent that substantially inactivates both the signal generator and the enzyme in the course of a photoreaction is applied to the sample, together with an optional additive which prevents target modification during photoactivated chemical bleaching. The method also includes an optional separate step of inactivating the enzyme. The step of enzyme inactivation may comprise, e.g., application of an enzyme inactivation reagent. The method further includes binding at least one subsequent probe having a binder coupled to an enzyme to one or more target present in the sample. The method further includes reacting the bound probe with an enzyme substrate coupled to a signal generator and observing a signal from the signal generator. In some embodiments, the method includes a step of washing the sample with a wash solution that effectively removes residual electron transfer reagents from the sample. In some embodiments, the wash solution contains ethanol.

In yet other embodiments, the method includes the steps of providing a biological sample including multiple targets and binding at least one probe to one or more target present in the sample. The method further includes detecting a signal from the bound probe. The bound probe is contacted with an electron transfer reagent and an optional additive which prevents target modification, and the sample comprising the bound probe, the additive and the electron transfer reagent is irradiated, thereby bleaching the probe. The method further includes binding at least one subsequent probe to one or more target present in the sample followed by detecting a signal from the subsequent bound probe. In some embodiments, the method includes a step of washing the sample with a wash solution that effectively removes residual electron transfer reagents from the sample. In some embodiments, the wash solution contains ethanol.

In yet other embodiments, the method includes the steps of providing a biological sample including multiple targets and binding at least one fluorescent probe to one or more target present in the sample. The method further includes binding at least one control probe to one or more target in the sample. The bound probe is contacted with an electron transfer reagent and an optional additive which prevents target modification, and the sample comprising the bound probe, the additive and the electron transfer reagent is irradiated, thereby bleaching the probe and not the control probe. The method further includes binding at least one subsequent probe to one or more target present in the sample followed by detecting a signal from the subsequent bound probe. In some embodiments, the method includes a step of washing the sample with a wash solution that effectively removes residual electron transfer reagents from the sample. In some embodiments, the wash solution contains ethanol.

In yet other embodiments, the methods described above provide a series of at least two images depicting optically labeled biological targets.

Biological Samples

A biological sample in accordance with one embodiment of the invention may be solid or fluid. Suitable examples of biological samples may include, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Cell cultures may include mixed cell culture, stem cell colonies or cultures derived from various cancer or primary cell lines. In some embodiments, the biological sample may be analyzed as is, that is, without harvest and/or isolation of the target of interest. In an alternative embodiment, harvesting and isolation of targets may be performed prior to analysis. In some embodiments, the methods disclosed herein may be particularly suitable for in vitro analysis of biological samples.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

In some embodiments, a biological sample may include a tissue sample or section, a whole cell, a cell constituent, e.g., cell organelle, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseased tissue samples (e.g., tissue section from colon, breast tissue, prostate). A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, tissue microassay may be used. In some embodiments, the same section of tissue sample may be analyzed with respect to at least five different targets (at morphological or molecular level). In some embodiments, the same section of tissue sample may be analyzed with respect to greater than five different targets (at morphological or molecular level). In some embodiments, the same section of tissue sample may be analyzed at both morphological and molecular levels.

A tissue section, if employed as a biological sample may have a thickness in a range that is less than about 100 micrometers, in a range that is less than about 50 micrometers, in a range that is less than about 25 micrometers, or in range that is less than about 10 micrometers.

In some embodiments, the biological sample may comprise one or more of proteins, carbohydrates or nucleic acids. In some embodiments, a biological sample or the targets in the biological sample may be adhered to a solid support. A solid support may include microarrays (e.g., DNA or RNA microarrays), gels, blots, glass slides, beads, or ELISA plates. In some embodiments, a biological sample or the targets in the biological sample may be adhered to a membrane selected from nylon, nitrocellulose, and polyvinylidene difluoride. In some embodiments, the solid support may include a plastic surface selected from polystyrene, polycarbonate, and polypropylene.

Targets

A target may be present on the surface of a biological sample (for example, an antigen on a surface of a tissue section) or present in the bulk of the sample (for example, an antibody in a buffer solution). In some embodiments, a target may not be inherently present on the surface of a biological sample and the biological sample may have to be processed to make the target available on the surface (e.g., antigen recovery, enzymatic digestion, epitope retrieval, or blocking). In some embodiments, the target may be present in a body fluid such as blood, blood plasma, serum, or urine. In some other embodiments, the target may be fixed in a tissue, either on a cell surface, or within a cell.

Suitability of targets to be analyzed may be determined by the type and nature of analysts required for the biological sample. In some embodiments, a target may provide information about the presence or absence of an analyte in the biological sample. In another embodiment, a target may provide information on a state of a biological sample. For example, if the biological sample includes a tissue sample, the methods disclosed herein may be used to detect targets that may help in comparing different types of cells or tissues, comparing different developmental stages, detecting the presence of a disease or abnormality, or determining the type of disease or abnormality.

Targets may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may essentially include proteins or nucleic acids. In other embodiments, multiple types of targets, e.g., nucleic acids, polysaccharides, lipids, enzymes, enzyme substrates, ligands, receptors, antigens or haptens may be detected and/or analyzed in the same biological sample in one or multiple cycles. One or more of the aforementioned targets may be characteristic of particular cells, while other targets may be associated with a particular disease or condition. In some embodiments, targets that may be detected and analyzed using the methods disclosed herein may include, but are not limited to, prognostic targets, hormone or hormone receptor targets, lymphoid targets, tumor targets, cell cycle associated targets, neural tissue and tumor targets, or cluster differentiation targets.

Suitable examples of prognostic targets may include enzymatic targets such as galactosyl transferase II, neuron specific enolase, proton ATPase-2, or acid phosphatase.

Suitable examples of hormone or hormone receptor targets may include human chorionic gonadotropin (HCG), adrenocorticotropic hormone, carcinoembryonic antigen (CEA), prostate-specific antigen (PSA), estrogen receptor, progesterone receptor, androgen receptor, gClq-R/p33 complement receptor, IL-2 receptor, p75 neurotrophin receptor, PTH receptor, thyroid hormone receptor, or insulin receptor.

Suitable examples of lymphoid targets may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, Immunoglobulin G, Immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor targets may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC Glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibits peptide, PTEN, renal cell carcinoma target, small intestinal mucinous antigen, tetranectin, thyroid transcription factor-1, tissue inhibitor of matrix metalloproteinase 1, tissue inhibitor of matrix metalloptoteinase 2, tyrosinase, tyrosinase-related protein-1, villin, or von Willebrand factor.

Suitable examples of cell cycle associated targets may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1 minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor targets may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD36, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw143, CD146, CD147, CD148, CDw149, CDw150, CD151 CD152, CD153, CD154, CD155, CD156, CD157, CD158a, CD158b, CD161, CD162, CD163, CD164, CD165, CD166, and TCR-zeta.

Other suitable prognostic targets may include centromere protein-F (CENP-F), giantin, involucrin, lamin A&C (XB 10), LAP-70, mucin, nuclear pore complex proteins, p180 lamellar body protein, ran, r, cathepsin D, Ps2 protein, Her2-neu, P53, S100, epithelial target antigen (EMA), TdT, MB2, MB3, PCNA, or Ki67.

Probes

As defined previously, the probe refers to an agent having a binder and a label, such as a signal generator or an enzyme.

In some embodiments, a binder and a label (signal generator or an enzyme) may be coupled to each other directly (that is without any linkers). In other embodiments, a binder and a label (signal generator or an enzyme) may be coupled to each other via a linker. As used herein, "coupled" generally refers to two entities (for example, binder and signal generator) stably bound to one another by any physicochemical means. The nature of the coupling may be such that it does not substantially impair the effectiveness of either entity. A binder and a label may be coupled to each other through covalent or non-covalent interactions. Non-covalent interactions may include, but are not limited to, hydrophobic interactions, ionic interactions, hydrogen-bond interactions, high affinity interactions (such as, biotin-avidin or biotin-streptavidin complexation), or other affinity interactions.

In some embodiments, a binder and a label (signal generator or an enzyme) may be chemically linked to each other through functional groups capable of reacting and forming a linkage under suitable conditions. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioesters; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones, hydroxyamine and aldehydes or ketones, imido ester and amines or anilines; isocyanate and amines or anilines; and isothiocyanate and amines or anilines. A functional group in one of the aforementioned functional group pair may be present in a binder and a corresponding functional group may be present in the signal generator or the enzyme. For example, a binder may include a carboxylic acid and the signal generator or the enzyme may include an amine, aniline, alcohol or acyl halide, or vice versa. Conjugation between the binder and the signal generator or the enzyme may be effected in this case by formation of an amide or an ester linkage.

In some embodiments, the binder may be intrinsically labeled with a signal generator (for example, if the binder is a protein, during synthesis using a detectably labeled amino acid) or an enzyme (for example, if the binder is an enzyme). A binder that is intrinsically labeled may not require a separate signal generator or an enzyme in order to be detected. Rather the intrinsic label may be sufficient for rendering the probe detectable. In alternate embodiments, the binder may be labeled by binding to it a specific signal generator or an enzyme (i.e., extrinsically labeled).

In some embodiments, the binder and the label (signal generator or the enzyme) are embodied in a single entity. In alternative embodiments, the binder and the label (signal generator or the enzyme) are embodied in discrete entities (e.g., a primary antibody capable of binding a target and an enzyme or a signal generator-labeled secondary antibody capable of binding the primary antibody or a hapten labeled primary antibody capable of binding a target and an enzyme or a signal generator-labeled anti-hapten antibody capable of binding the hapten labeled primary antibody). When the binder and the signal generator or the enzyme are separate entities they may be applied to a biological sample in a single step or multiple steps. In some embodiments, the binder and the label (signal generator or the enzyme) are separate entitles that are pre-attached before application to the biological sample and applied to the biological sample in a single step. In yet other embodiments, the binder and the label (signal generator or the enzyme) are separate entitles that are applied to the biological sample independently and combine following application.

Binders

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

In some embodiments, binding between the target and the binder may be affected by physical binding. Physical binding may include binding effected using non-covalent interactions. Non-covalent interactions may include, but are not limited to, hydrophobic interactions, ionic interactions, hydrogen-bond interactions, or affinity interactions (such as, biotin-avidin or biotin-streptavidin complexation). In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten: nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibtor, or vitamin B12/intrinsic factor. Other suitable examples of binding pairs may include complementary nucleic acid fragments (including DNA sequences, RNA sequences, LNA sequences, and PNA sequences or other modified nucleic acids known in the literature); Protein A/antibody; Protein G/antibody; nucleic acid/nucleic acid binding protein; or polynucleotide/polynucleotide binding protein.

In some embodiments, the binder may be a sequence or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be its overall three dimensional structure. A quaternary structure of a target may be the structure formed by its noncovalent interaction with one or more other targets or macromolecules (such as protein interactions). An example of a quaternary structure may be the structure formed by the four-globin protein submits to make hemoglobin. A binder in accordance with the embodiments of the invention may be specific for any of the afore-mentioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to a target antigen.

In some embodiments, a biological sample may include a cell or a tissue sample and the methods disclosed herein may be employed in immunohistochemistry (IHC). Immunochemistry may involve binding of a target antigen to an antibody-based binder to provide information about the tissues or cells (for example, diseased versus normal cells). Examples of antibodies (and the corresponding diseases/disease cells) suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD13 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblastic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T.B., and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salivary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, and proliferating cell nuclear antigen, clone pc10 (Sigma Aldrich, P8825); anti smooth muscle alpha actin (SmA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

In some embodiments, a binder may be sequence-specific. A sequence-specific binder may include a nucleic acid and the binder may be capable of recognizing a particular linear arrangement of nucleotides or derivatives thereof in the target. In some embodiments, the linear arrangement may include contiguous nucleotides or derivatives thereof that may each bind to a corresponding complementary nucleotide in the binder. In an alternate embodiment, the sequence may not be contiguous as there may be one, two, or more nucleotides that may not have corresponding complementary residues on the probe. Suitable examples of nucleic acid-based binders may include, but are not limited to, DNA or RNA oligonucleotides or polynucleotides. In some embodiments, suitable nucleic acids may include nucleic acid analogs, such as dioxygenin dCTP, biotin dCTP 7-azaguanosine, azidothymidine, inosine, or uridine.

In certain embodiments, both the binder and the target may include nucleic acids. In some embodiments, a nucleic-acid based binder may form a Watson-Crick bond with the nucleic acid target. In another embodiment, the nucleic acid binder may form a Hoogsteen bond with the nucleic acid target, thereby forming a triplex. A nucleic acid binder that binds by Hoogsteen binding may enter the major groove of a nucleic acid target and hybridizes with the bases located there. Suitable examples of the above binders may include molecules that recognize and bind to the minor and major grooves of nucleic acids (for example, some forms of antibiotics.) In certain embodiments, the nucleic acid binders may form both Watson-Crick and Hoogsteen bonds with the nucleic acid target (for example, bis PNA probes are capable of both Watson-Crick and Hoogsteen binding to a nucleic acid).

The length of nucleic acid binder may also determine the specificity of binding. The energetic cost of a single mismatch between the binder and the nucleic acid target may be relatively higher for shorter sequences than for longer ones. In some embodiments, hybridization of smaller nucleic acid binders may be more specific than the hybridization of longer nucleic acid probes, as the longer probes may be more amenable to mismatches and may continue to bind to the nucleic acid depending on the conditions. In certain embodiments, shorter binders may exhibit lower binding stability at a given temperature and salt concentration. Binders that may exhibit greater stability to bind short sequences may be employed in this case (for examples, bis PNA). In some embodiments, the nucleic acid binder may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid binder may have a length in a range that is greater than about 1000 nucleotides. Notwithstanding the length of the nucleic acid binder, all the nucleotide residues of the binder may not hybridize to complementary nucleotides in the nucleic acid target. For example, the binder may include 50 nucleotide residues in length, and only 25 of those nucleotide residues may hybridize to the nucleic acid target. In some embodiments, the nucleotide residues that may hybridize may be contiguous with each other. The nucleic acid binders may be single stranded or may include a secondary structure. In some embodiments, a biological sample may include a cell or a tissue sample and the biological sample may be subjected to in-situ hybridization (ISH) using a nucleic acid binder. In some embodiments, a tissue sample may be subjected to in situ hybridization in addition to immunohistochemistry (IHC) to obtain desired information from the sample.

Regardless of the type of binder and the target, the specificity of binding between the binder and the target may also be affected depending on the binding conditions (for example, hybridization conditions in case of complementary nucleic acids). Suitable binding conditions may be realized by modulating one or more of pH, temperature, or salt concentration.

A binder may be intrinsically labeled (signal generator or enzyme attached during synthesis of binder) or extrinsically labeled (signal generator or enzyme attached during a later step). For example for a protein-based binder, an intrinsically labeled binder may be prepared by employing labeled amino acids. Similarly, an intrinsically labeled nucleic acid may be synthesized using methods that incorporate signal generator-labeled nucleotides or signal generator labeled nucleoside phosphoramidites directly into the growing nucleic acid depending upon the method used for nucleic acid synthesis. In some embodiments, a binder may be synthesized in a manner such that signal generators or enzymes may be incorporated at a later stage. For example, this latter labeling may be accomplished by chemical means by the introduction of active amino or thiol groups into nucleic acids or peptide chains. In some embodiments, a binder such as a protein (for example, an antibody) or a nucleic acid (for example, a DNA) may be directly chemically labeled using appropriate chemistries.

In some embodiments, combinations of binders may be used that may provide greater specificity or in certain embodiments amplification of the signal. Thus, in some embodiments, a sandwich of binders may be used, where the first binder may bind to the target and serve to provide for secondary binding, where the secondary binder may or may not include a label, which may further provide for tertiary binding (if required) where the tertiary binding member may include a label.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse Anti-Express™ for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for .alpha.-D-galactose; and melibiose for carbohydrate-binding proteins, sugars, nickel couple matrix or heparin.

In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a signal generator or an enzyme before binding to the primary antibody or may be capable of binding to a signal generator or an enzyme at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In some embodiments, the methods disclosed herein may be employed in an immunostaining procedure, and a primary antibody may be used to specifically bind the target protein. A secondary antibody may be used to specifically bind to the primary antibody, thereby forming a bridge between the primary antibody and a subsequent reagent (for example a signal generator or enzyme), if any. For example, a primary antibody may be mouse IgG (an antibody created in mouse) and the corresponding secondary antibody may be goat anti-mouse (antibody created in goat) having regions capable of binding to a region in mouse IgG.

In some embodiments, signal amplification may be obtained when several secondary antibodies may bind to epitopes on the primary antibody. In an immunostaining procedure a primary antibody may be the first antibody used in the procedure and the secondary antibody may be the second antibody used in the procedure. In other embodiments a third antibody may be used to further increase signal. For example, an antibody raised in mouse may be used to bind the target. A goat-anti-mouse secondary antibody may be used to bind the primary antibody and a labeled donkey-anti-goat antibody may be used as a tertiary antibody to bind to the secondary antibodies already bound to the primary antibody which itself is bound to the target. In some embodiments, a primary antibody may be the only antibody used in an immunostaining procedure.

Signal Generators

The type of signal generator suitable for the methods disclosed herein may depend on a variety of factors, including the nature of the analysis being conducted, the type of the energy source and detector used, the type of electron transfer reagent employed, the type of hinder, the type of target.

A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a binder. Additionally, a suitable signal generator may not interfere with the binding of the binder to the target, nor may it significantly affect the binding specificity of the binder. A suitable signal generator may be organic or inorganic in nature. In some embodiments, a signal generator may be of a chemical, peptide or nucleic acid nature.

A suitable signal generator may be directly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength.

A signal generator, suitable in accordance with the methods disclosed herein may be amenable to manipulation on application of an electron transfer reagent. In some embodiments, a signal generator may be capable of being bleached, e.g., the signal it generates may be diminished or destroyed as result of the signal generator being modified in the course of a photoreaction. Chemical modification may include complete disintegration of the signal generator or modification of the signal-generating component of the signal generator. In some embodiments, the signal generator is charged.

Modification of the signal-generating component may include any chemical modification (such as addition, substitution, or removal) that may result in the modification of the signal generating properties. For example, unconjugating a conjugated signal generator may result in destruction of chromogenic properties of the signal generator. Similarly, substitution of a fluorescence-inhibiting functional group on a fluorescent signal generator may result in modification of its fluorescent properties. In some embodiments, one or more signal generators substantially resistant to inactivation by a specific chemical agent may be used as a control probe in the provided methods.

In some embodiments, a signal generator may be selected from a light emissive molecule, a radioisotope (e.g., $P^{32}$ or $H^3$, $^{14}C$, $^{125}I$ and $^{131}I$), an optical or electron density marker, a Raman-active tag, an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle.

In some embodiments, a signal generator may be an optical signal generator, e.g., may include a light-emissive molecule. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence. Non-limiting examples of optical signal generators include a fluorescent signal generator, e.g., a fluorophore, a Raman-active tag or a chromophore.

In some embodiments, a signal generator may essentially include a fluorophore. In some embodiments, a signal generator may essentially include a fluorophore attached to an antibody, for example, in an immunohistochemistry analysis. Suitable fluorophores that may be conjugated to a primary antibody include, but are not limited to, Fluorescein, Rhodamine, Texas Red, VECTOR Red, ELF (Enzyme-Labeled Fluorescence), Cy2, Cy3, Cy3.5, Cy5, Cy7, Fluor X, Calcein, Calcein-AM, CRYPTOFLUOR, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY, boron dipyrromethene difluoride, 1,3-dichloro-7-hydroxy-9,9-dimethyl-2(9H)-Acridinone (DDAO), dimethylacridinone (DAO), Oregon Green, MITOTRACKER Red, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, Infra-Red (IR) Dyes, Cyclic GDP-Ribose (cGDPR) Calcofluor White, Lissamine, Umbelliferone, Tyrosine or Tryptophan. In some embodiments, the fluorophore can be cyanine, rhodamine, coumarins or pyrelium dyes. In some embodiments, a signal generator may essentially include a cyanine dye. In further embodiments, a signal generator may essentially include one or more of a Cy2 dye, a Cy3 dye, a Cy5 dye, or a Cy7 dye. In alternative embodiments, the signal generator may be BODIPY, rhodamine, 1,3-dichloro-7-hydroxy-9,9-dimethyl-2(9H)-Acridinone (DDAO) or 7-hydroxy-9,9-dimethyl-2(9H)-Acridinone (DAO).

In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

As described hereinabove, one or more of the aforementioned molecules may be used as a signal generator. In some embodiments, one or more of the signal generators may be amenable to signal destruction and the signal generator may essentially include a molecule capable of being bleached by photoactivated chemical bleaching. In some embodiments, a signal generator may include a fluorophore capable of being chemically modified in a photoreaction that also involves an electron transfer reagent and irradiation. In some embodiments, a signal generator may essentially include cyanine, BODIPY, rhodamine, or acridinone (e.g., DDAO and DAO), that can be modified in a photoreaction that also involves addition of an electron transfer reagent and irradiation. In some embodiments, a signal generator may include one or more of a Cy2 dye, a Cy3 dye, a Cy5 dye, or a Cy7 dye that can be bleached by photoactivated chemical bleaching.

Enzyme and Enzyme Substrates

In some embodiments, a probe may include a birder coupled to an enzyme. In some embodiments, a suitable enzyme catalyzes a chemical reaction of the substrate to form a reaction product that can bind to a receptor (e.g., phenolic groups) present in the sample. A receptor may be exogenous (that is, a receptor extrinsically adhered to the sample or the solid-support) or endogenous (receptors present intrinsically in the sample or the solid-support). Signal amplification may be effected as a single enzyme may catalyze a chemical reaction of the substrate to covalently bind multiple signal generators near the target.

In some embodiments, a suitable enzyme may also be capable of being inactivated in the course of a photoreaction. Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase. In some embodiments, the enzyme is a peroxidase selected from horseradish peroxidase, cytochrome C peroxidase, glutathione peroxidase, microperoxidase, myeloperoxidase, lactoperoxidase, and soybean peroxidase.

In some embodiments, an enzyme is not inactivated in the course of a photoreaction, but is inactivated in a separate inactivation step carried out before or after the photoreaction is completed. The inactivation step may include application of an enzyme inactivation reagent to the sample including the enzyme.

In some embodiments, a binder and an enzyme may be embodied in a single entity, for example a protein molecule capable of binding to a target and also catalyzing a chemical reaction of substrate. In other embodiments, a binder and an enzyme may be embodied in separate entities and may be coupled by covalent bond formation or by using ligand-receptor conjugate pairs (e.g., biotin streptavidin).

An enzyme substrate may be selected depending on the enzyme employed and the target available for binding in the sample. For example, in embodiments including HRP as an enzyme, a substrate may include a substituted phenol (e.g., tyramine). Reaction of HRP to the tyramine may produce as activated phenolic substrate that may bind to endogeneous receptors like electron-rich moieties (such as tyrosine or tryptophan) or phenolic groups present in the surface proteins of a biological sample. In alternate embodiments, where 3-methyl-2-benzothiazolinone hydrochloride (MBTH) may be employed as a substrate along with an HRP enzyme, exogenous receptors like p-dimethylaminobenzaldehyde (DMAB) may be adhered to the solid support or the biological sample before reacting with the substrate.

In some embodiments, an enzyme substrate may be dephosphorylated after reaction with the enzyme. The dephosphorylated reaction product may be capable of binding to endogeneous or exogenous receptors (e.g., antibodies) in the sample or the solid-support. For example, an enzyme may include alkaline phosphatase (AP) and a substrate may include NADP, substituted phosphates (e.g., nitrophenyl phosphate), or phosphorylated biotin. The receptors may include NAD binding proteins, antibodies to the dephosphorylated reaction product (e.g., anti nitro-phenol), avidin, or streptavidin accordingly. In some embodiments, a substrate may produce insoluble product upon action of the enzyme which may deposit in vicinity of where they are generated. Non-limiting examples of such substrates may include diaminobezidine (DAB) for HRP and ELF for AP.

In some embodiments, an enzyme may include β-galactosidase and a substrate may include β-galactopyranosyl-glycoside of fluorescein or coumarin. Receptors may include antibodies to deglycosylated moieties (e.g., anti-fluorescein or anti-coumarin). In some embodiments, multiple enzyme combinations like HRP/AP may be used as an enzyme. A substrate may include phosphorylated substituted phenol e.g., tyrosine phosphate, which may be dephosphorylated by AP before reacting with HRP to form a reaction product capable of binding to phenolic groups or electron rich moieties-based receptors.

A reaction product of the enzyme substrate may further be capable of providing a detectable signal. In some embodiments, enzyme substrates employed in the methods disclosed herein may include non-chromogenic or non-chemiluminescent substrates, that is a reaction of the enzyme and the enzyme substrate may not itself produce a detectable signal. Enzyme substrates employed in the methods disclosed herein may include an extrinsic signal generator (e.g., a fluorophore) as a label. The signal generator and the enzyme substrate may be attached directly (e.g., an enzyme substrate with a fluorescent label) or indirectly (e.g., through ligand-receptor conjugate pair). In some embodiments, a substrate may include protected functional groups (e.g., sulfhydryl groups). After binding of the activated substrate to the receptors, the functional group may be deprotected and conjugation to a signal generator effected using a signal generator having a thiol reactive group (e.g., maleimide or iodoacetyl).

In some embodiments, a probe may include horseradish peroxidase and the substrate is selected from substituted phenols (e.g., tyramine). In some embodiments, the horseradish peroxidase causes the activated phenolic substrate to covalently bind to phenolic groups present in the sample. In some embodiments, a probe may include a binder coupled to HRP and a substrate may include tyramine-coupled to a fluorophore.

Electron Transfer Reagents and Photoreaction

An electron transfer reagent may include one or more chemicals that can engage in a photoreaction with a molecule capable of undergoing photoexcitation. The molecule capable of undergoing photoexcitation may be a signal generator. An electron transfer reagent may be contacted with the sample in the form of a solid, a solution, a gel, or a suspension.

In some embodiments, an electron transfer reagent may include a borate salt. In some embodiments, the borate salt is represented by the following structural formula:

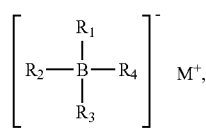

wherein:
each $R_1$, $R_2$, and $R_3$ is, independently, an alkyl, an alkenyl, an akynyl an aryl or a heteroaryl, wherein the alkyl, alkenyl, alkynyl, aryl or heteroaryl is optionally substituted with one or mere substituents selected from the group consisting of (C1-C4)alkyl, (C1-C4)alkoxy, (C1-C4)alkylamino, amino, hydroxyl, cyano, halogen, or nitro.

$R_4$ is an alkyl, an alkenyl, or an akynyl wherein the alkyl, alkenyl or alkynyl is optionally substituted with one or more substituents selected from the group consisting of (C1-C4)alkyl, (C1-C4)alkoxy, (C1-C4)alkylamino, amino, hydroxyl, cyano, halogen, or Nitro, and $M^+$ is selected from the group consisting of inorganic cations and organic cations.

In some embodiments, $M^+$ is selected from the group of inorganic cations, e.g., $Li^+$, $Na^+$, or $K^+$. In other embodiments, $M^+$ is selected from the group of organic cations. Non-limiting examples of organic cations can include $NR_4^+$, wherein each R is independently hydrogen, a substituted or unsubstituted alkyl group (e.g., a hydroxyalkyl group, aminoalkyl group or ammoniumalkyl group) or substituted or unsubstituted aryl group (e.g., phenyl, naphthyl, and anthracyl, imidazolyl, thienyl, furanyl, pyridyl, pyrimidyl, pyranyl, pyrazolyl, pyrroyl, pyrazinyl, thiazole, oxazolyl, and tetrazole).

In some embodiments, each $R_1$, $R_2$, and $R_3$ is aryl. In some embodiments, the aryl is phenyl. In some embodiments, the phenyl is an unsubstituted phenyl.

In some embodiments, $R_4$ is an optionally substituted alkyl. In some embodiments, $R_4$ is unsubstituted butyl.

In some embodiments, each $R_1$, $R_2$, and $R_3$ is an optionally substituted aryl and $R_4$ is an optionally substituted alkyl. In a further embodiment, each $R_1$, $R_2$, and $R_3$ is unsubstituted phenyl and $R_4$ is unsubstituted butyl, and the borate salt is triphenylbutyl borate salt.

In some embodiments, the electron transfer reagent is a high water solubility borate salt. A high water solubility borate is a borate that can be substantially removed from the sample after signal bleaching by simple PBS washes without the addition of an enabler. In some embodiments, the high solubility borate is a tetraalkyl borate with small alkyl groups C3-C5. In some embodiments the high water solubility borates have hydrophilic functionalities on the alkyl or aryl groups of the borate salt. In some embodiments the hydrophilic groups are short oligomeric polyethylene glycol chains. In some embodiments the aqueous solubility of the high water solubility borate is >20 mM.

In some embodiments, $M^+$ is an inorganic cation. In some embodiments, the inorganic cation is $Li^+$, $Na^+$ or $K^+$. In one embodiment, $M^+$ is $Li^+$.

Other suitable electron transfer reagents may include sulfinates, enolates, carboxylates (e.g., ascorbic acid), organometallics and amines (e.g., triethanolamine, and N-phenylglycine). These and other electron transfer reagents have been previously described (see, e.g., *Macromolecules* 1974, 7, 179-187; *Photogr. Sci. Eng.* 1979, 23, 150-154; *Topics in Current Chemistry*, Mattay, J., Ed.; Springer-Verlag: Berlin, 1990, Vol. 156, pp 199-225; and *Pure Appl. Chem.* 1984, 56, 1191-1202.)

An electron transfer reagent to be used for photoactivated chemical bleaching is chosen such that the photoreaction between the electron transfer reagent and a signal generator is energetically favorable. In some embodiments, the electron transfer reagent and the photoexcited signal generator form an electron donor/acceptor pair, wherein art transfer from the electron transfer reagent to the signal generator is energetically favorable. The electron transfer may further lead to chemical modification of the signal generator, resulting in bleaching of the signal generator. Examples of electron transfer reagents and signal generators that can form electron donor/acceptor pairs include triaryl alkyl borates, such as triphenyl butyl borate as an electron transfer reagent and cyanine dyes (e.g., Cy3 and Cy5), BODIPY, rhodamine or acridone dyes as signal generators.

One or more of the aforementioned electron transfer reagents may be used in the methods disclosed herein, in combination with the additive which prevents target modification, depending upon susceptibility of the signal generator, of the binder, of the enzyme, of the target, or of the biological sample to photoexcitation and/or subsequent photoreaction with the electron transfer reagent. In some embodiments, photoexcitation of the signal generator by irradiation and subsequent photoreaction between the electron transfer reagent and the photoexcited signal generator, in the presence of the additive which prevents target modification, essentially does not affect the integrity of the binder, the target, and the biological sample. In some embodiments, photoexcitation of the signal generator by irradiation and subsequent photoreaction, in the presence of the additive which prevents target modification, does not affect the specificity of binding between the binder and the target.

In some embodiments, where two or more (up to 5) signal generators may be employed simultaneously, a photoreaction may be capable of selectively modifying one or more signal generators. This selectivity may be derived from selective photoexcitation of the signal generator by irradiation at specific wavelength. The irradiation wavelength is chosen such that one or more signal generator may be photoexcited, while the remaining one or more signal generator that may be present in a sample may remain unaffected. In some embodiments, irradiation limited to a range of wavelengths between 520-580 nm can be used for selective photoexciation of Cy3 dye. In other embodiments, irradiation limited to a range of wavelengths between 620-680 nm can be used for selective photoexcitation of a Cy5 dye. In alternative embodiments, selective photoexcitation may be accomplished by using a laser.

The propensity of photoexcited signal generators to further undergo photoreaction may depend on the choice of the electron transfer reagent, as discussed above, as well as on the reaction conditions, such as temperature, solvent and pH.

In some embodiments, the photoactivated chemical bleaching is carried out at a temperature of 4-50° C. more preferably, at a temperature of 20-30° C.

In some embodiments, the photoactivated chemical bleaching is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

Additives which Prevent Target Modification

Additives which prevent target modification include free radical scavengers and singlet oxygen quenchers. The use of additives further improve the photoactivated chemical bleaching technology due to improved sample integrity thus allowing multiple rounds of staining, imaging, bleaching and restaining which enables scanning of many biomarker targets that would allow quantitative analysis of multiple biomarkers in a single biological sample, such as a tissue section, without alteration of biomarker detectability.

The mechanism of photoactivated chemical bleaching is based on electron transfer between the excited dye (acceptor) and the electron transfer reagent (donor) followed by addition of a radical from the electron transfer reagent to the dye molecule which results in chemical modification of the dye to a non-fluorescent species. This method generates radical intermediates that, in addition to quenching the dye, react with, e.g., some protein epitopes, unsaturated lipids or DNA bases making their detection less robust in subsequent rounds. Another potential issue is the generation of highly reactive singlet oxygen species via photoexcitation of the fluorescent dye molecule, which can also destroy targets. Radical and singlet oxygen quenchers are used to scavenge any radical or reactive oxygen species that diffuse away from the dye vicinity thereby preventing any target modification. Dye is still quenched as the electron transfer only happens when the electron transfer reagent and dye are close to each other and hence the radicals are generated in the vicinity of the dye and can easily react with the dye. Similarly any singlet oxygen or other reactive oxygen species generated during the dye excitation has a possibility of destroying the dye before it diffuses away and interacts with the singlet oxygen/radical quenchers. A reduction of antigen effects in the presence of radical and singlet oxygen scavengers is achieved compared to photoactivated chemical bleaching in the absence of such scavenger additives.

Antioxidants or free radical scavengers refer to any additives that react directly with a variety of radicals, including the peroxy radical (ROO.), $CCl_3.$, and HO. as well as the superoxide radical ($O_2.'$). Examples of such additives are but not limited to, Vitamin C (Ascorbic acid), n-propyl gallate, mercaptoethanol, cysteine hydrochloride, t-butyl hydroxy toluene (BHT), Cycloheptatriene (CHT), dioctyl phthalate (DOP), 1,4-Dihydro-o-toluamide (TA), Vitamin E (a-tocopherol) and trolox.

Singlet oxygen is another type of reactive oxygen species that is generated by triplet sensitization of fluorophores. Not all free radical scavengers/quenchers are effective against singlet oxygen but some free radicals quenchers can effectively quench singlet oxygen, For example, antioxidants such as a-tocopherol and ascorbic acid can also act as singlet oxygen scavenger. Some quenchers such as curcumin and DABCO are great singlet oxygen quencher, while not effective against free radicals.

In certain embodiments, the additives which prevent target modification include inorganic compounds. These include basic inorganic salts such as carbonate, bicarbonate, permanganate, iodide, nitrate, ferrocyaninde, chloride salts, that scavenge hydrogen, hydroxyl radicals. In yet other embodiments these inorganic compounds may include transition metal salts or complexes containing metal ions such as Fe(II), Co(II), Mn(II) and Ru(II), which can bind to and react with NO and/or reactive oxygen species (ROS). In certain embodiments, the additives which prevent target modification include NO scavengers, such as iron complexes with dithiocarbamates or ruthenium compounds with polyamine-polycarboxylate scaffolds. In other embodiments, inorganic additives include metal cofactors such as selenium, iron, Manganese, zinc or copper and the corresponding antioxidant enzymes, such as superoxide dismutases, glutathione reductase, catalase, etc.

The chemical structure of some of the additives are illustrated here:

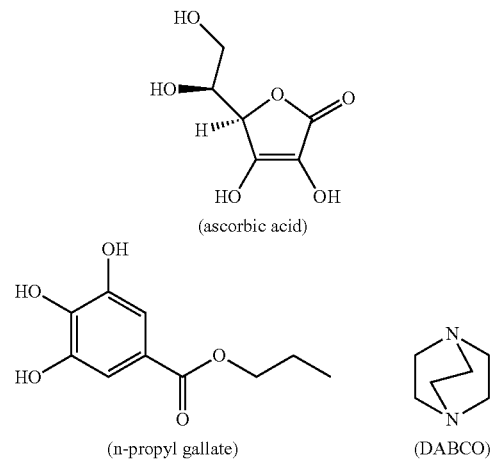

(ascorbic acid)

(n-propyl gallate)          (DABCO)

The use of radical or singlet oxygen quenchers (i.e., additives) during the photoactivated chemical bleaching preserves immunogenicity of biological samples for restaining of additional targets. This is achieved by adding one or more radical/singlet oxygen/reactive oxygen species scavengers to the electron transfer reagent before the stained slide is exposed to light in this mixture. An exemplary process involves illumination with UV or visible light (300-700 nm wavelength) onto a transparent container that includes the aqueous solution of electron transfer reagent (e.g., triakylarylborates) and radical scavenger/singlet oxygen scavenger additives into which a glass slide that supports tissues stained with fluorescent biomarker is immersed. The photons from the electron transfer reagent directly excite the fluorescent dye molecule and generate radicals and/or reactive oxygen species which react with and chemically modify the dye molecule, thereby quenching its fluorescence. The radicals which are not utilized to quench the dye and any singlet oxygen generated, although are capable of reacting with the targets, are effectively quenched by the scavenger additives.

Although the examples provided below relate to the bleaching of cyanine dyes, the use of scavengers is not restricted to these dyes. The scavengers quench the radicals generated after the fact or during the process of photoactivated chemical bleaching due to radical species generated by the dye-electron transfer reagent complex. Radical quenching with scavengers may compete with dye quenching depending upon the concentration of quencher used as well as the mechanism of electron transfer between the electron transfer reagent and the dye. When the dye quenching occurs by intramolecular electron transfer mechanism, chances of radicals generated reacting with dye are increased compared to an intermolecular electron transfer where the radicals may have a greater chance to diffuse away from the dye and react with either sample or radical quenchers. In certain embodiments, the concentration of the scavenger is lower than the concentration of the electron transfer reagent. In certain preferred embodiments, the concentration of the scavenger is at least ten times lower than the concentration of the electron transfer reagent. In certain more preferred embodiments, the concentration of the scavenger is at least a hundred times lower than the concentration of the electron transfer reagent.

In a preferred embodiment, the electron transfer reagent is borate salt such as triaryl alkyl borates, for example triphenyl butyl borate, and the signal generators include fluorescent dyes such as cyanine dyes (e.g., Cy3 and Cy5), BODIPY, rhodamine or acridone dyes.

Sequentially Analyzing a Biological Sample, Contacting and Binding the Probe

A biological sample may be contacted with a probe to bind the probe to a target in the biological sample. In some embodiments, a target may not be easily accessible for binding with the probe and a biological sample may be further processed to facilitate the binding between the target and the binder in the probe, for example through antigen recovery, enzymatic digestion, epitope retrieval, or blocking.

In some embodiments, a probe may be contacted with the biological sample in the form of a solution. In some embodiments, a probe may include a binder coupled to a label (signal generator or an enzyme). The binder and the label (signal generator or enzyme) may be embodied in a single molecule and the probe solution may be applied in a single step. Alternatively, the binder and the label (signal generator or enzyme) may be distinct entities and the probe solution may be applied in a single step or multiple steps. In all embodiments, a control probe may further be bonded to one or more targets in the sample.

Depending on the nature of the binder, the target, and the binding between the two, sufficient contact time may be allowed. In some embodiments, an excess of probe molecules (and accordingly binder molecules) may be employed to ensure all the targets in the biological sample are bound. After a sufficient time has been provided for the binding action, the sample may be contacted with a wash solution (for example, an appropriate buffer solution) to wash away any unbound probes. Depending on the concentration and type of probes used, a biological sample may be subjected to a number of washing steps with the same or different washing solutions being employed in each step.

In some embodiments, the biological sample may be contacted with more than one probe in the first binding step. The plurality of probes may be capable of binding different targets in the biological sample. For example, a biological sample may include two targets: target1 and target2 and two sets of probes may be used in this instance; probe1 (having binder1 capable of binding to target1) and probe2 (having binder2 capable of binding to target2). The plurality of probes may also comprise a plurality of multiple sets of target-binding probes. A plurality of probes may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

The number of probes that may be simultaneously bound to the target may depend on the type of detection employed, that is, the spectral resolution achievable. For example, for fluorescence-based signal generators, up to five different probes (providing up to five spectrally resolvable fluorescent signals) may be employed in accordance with the disclosed methods. Spectrally resolvable, in reference to a plurality of fluorescent signal generators, indicates that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems. In some embodiments all probes may be simultaneously bound but sequentially detected in sets of 1-5 probes per cycle.

In some embodiments, a biological sample may be essentially contacted with five or less than five probes in the first binding step. In embodiments employing enzyme-based probes, the number of probes that may be simultaneously bound to the target may also depend on the number of different enzymes and their corresponding substrates available.

In some embodiments, a biological sample may include a whole cell, a tissue sample, or the biological sample may be adhered to a microarray, a gel, or a membrane. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuemay. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by rising organic agents (such as, xylenes or gradually descending series of alcohols).

In some-embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer or Tris buffer or both in a sequential manner. In some embodiments, a tissue section may be optionally subjected to a blocking step to minimize any non-specific binding.

In some embodiments, the biological sample or a portion of the biological sample, or targets present in the biological sample may be adhered on the surface, e.g. DNA microarrays, or protein microarrays, or on the surface of solid supports (such as gels, blots, glass slides, beads, or ELISA plates). In some embodiments, targets present in the biological sample may be adhered on the surface of solid supports. Targets in the biological sample may be adhered on the solid support by physical bond formation, by covalent bond formation, or both.

In some embodiments, the targets in the biological sample may be adhered to membranes and probed sequentially using the methods disclosed herein. In some embodiments, targets in the biological sample may be processed before contacting the sample with the membrane. For example, embodiments involving methods for probing protein targets in a tissue sample may include the step of extracting the target proteins from a biological sample of tissue homogenate or an extract. Solid tissues or whole cells may be first broken down mechanically using a blender (for larger sample volumes), using a homogenizer (smaller volumes), or by sonication. Different cell compartments and organelles may be separated using filtration and centrifugation techniques. Detergents, salts, and buffers may also be employed to encourage lysis of cells and to solubilize proteins. Similarly, embodiments involving methods for probing nucleic acids, may include the step of preparing DNA or RNA fragments, for example using restriction endonucleases (for DNA).

In some embodiments, targets extracted from the biological sample may be further separated by gel electrophoresis. Separation of targets may be by isoelectric point (pI), molecular weight, electric charge, or a combination of these factors. The nature of the separation may depend on the treatment of the sample and the nature of the gel. A suitable gel may be selected from a polyacrylamide gel, an SDS-polyacrylamide gel, or an agarose gel.

A suitable membrane may be selected such that the membrane has non-specific target binding properties. In some embodiments, a suitable membrane may be selected from a polyvinylidene fluoride membrane, a nitrocellulose membrane, or a nylon membrane. In some embodiment, a suitable membrane may be selected such that the membrane may be substantially stable to multiple probing. In embodiments involving probing of targets using protein probes, the membranes may be blocked using a blocking solution to prevent non-specific binding of protein probes to the membranes. In embodiments involving probing of DNA fragments, the DNA gel may be treated with a dilute HCL solution or an alkaline solution to facilitate more efficient transfer of the DNA from the gel to the membrane.

In some embodiments, the membrane may be subjected to temperatures in a range of about 60° C. to about 100° C. to covalently bind the targets to the membrane, for example DNA targets to a nitrocellulose membrane. In some embodiments, the membrane may be exposed to ultraviolet radiation to covalently bind the targets to the membrane, for example DNA targets to a nylon membrane. In some embodiments, the targets in the biological sample may not be separated by electrophoresis before blotting on a membrane and may be probed directly on a membrane, for example, in dot blot techniques.

Following the preparation of the tissue sample or the membrane, a probe solution (e.g., labeled-antibody solution) may be contacted with the tissue section or the membrane for a sufficient period of time and under conditions suitable for binding of binder to the target (e.g., antigen). As described earlier, two detection methods may be used: direct or indirect. In a direct detection, a signal generator-labeled primary antibody (e.g., flourophore-labeled primary antibody or enzyme-labeled primary antibody) may be incubated with an antigen in the tissue sample or the membrane, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In some embodiments two or more (at most five) primary antibodies (from different species, labeled or unlabeled) may be contacted with the tissue sample. Unlabeled antibodies may be then contacted with the corresponding labeled secondary antibodies. In alternate embodiments, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In embodiments where the primary antibody or the secondary antibody may be conjugated to an enzymatic label, a fluorescent signal generator-coupled substrate may be added to provide visualization of the antigen. In some embodiments, the substrate and the fluorescent signal generator may be embodied in a single molecule and may be applied in a single step. In other embodiments, the substrate and the fluorescent signal generator may be distinct entities and may be applied in a single step or multiple steps.

An enzyme coupled to the binder may react with the substrate to catalyze a chemical reaction of the substrate to covalently bind the fluorescent signal generator-coupled substrate with the biological sample. In some embodiments, an enzyme may include horseradish peroxidase and the substrate may include tyramine. Reaction of the horseradish peroxidase (HRP) with the tyramine substrate may cause the tyramine substrate to covalently bind to phenolic groups present in the sample. In embodiments employing enzyme-substrate conjugates, signal amplification may be attained as one enzyme may catalyze multiple substrate molecules. In some embodiments, methods disclosed herein may be employed to detect low abundance targets using indirect detection methods (e.g., using primary-secondary antibodies), using HRP-tyramide signal amplification methods, or combinations of both (e.g., indirect HRP-tyramide signal amplification methods). Incorporation of signal amplification techniques into the methods disclosed herein and correspondingly the type of signal amplification techniques incorporated might depend on the sensitivity required for a particular target and the number of steps involved in the protocol.

Detecting a Signal from the Probe or from the First Set of the Plurality of Probes A signal from the signal generator may be detected using a detection system. The nature of the detection system used may depend upon the nature of the signal generators used. The detection system may include a charge coupled device (CCD) detection system, a fluorescent detection system, an electrical detection system, a photographic film detection system, a chemiluminescent detection system, an enzyme detection system, an optical detection system, a near field detection system, or a total internal reflection (TIR) detection system.

One or more of the aforementioned techniques may be used to detect one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded.

In some embodiments, the observed, and detected signal is a fluorescent signal, and a probe bound to a target in a biological sample may include a signal generator that is a fluorophore. In some embodiments, the fluorescent signal may be measured by determining fluorescence wavelength or fluorescent intensity using a fluorescence detection system. In some embodiments, a signal may be detected in situ, that is, a signal may be detected directly from the signal generator associated through the binder to the target in the biological sample. In some embodiments, a signal from the signal generator may be analyzed within the biological sample, obviating the need for separate array-based detection systems.

In some embodiments, detecting a signal may include capturing an image of the biological sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitalized image). The same procedure may be repeated for different signal generators (if present) that are bound in the sample using the appropriate flourescence filters.

In some embodiments, multiple different types of signals may be detected in the same sample. For example, one target may be detected with a fluorescent probe and a second target in the same sample may be detected with a chromogenic probe.

Applying an Electron Transfer Reagent and Irradiating to Initiate a Photoreaction to Modify the Signal To modify the signal, an electron transfer reagent may be applied to the sample, and the sample may subsequently be irradiated to initiate a photoreaction. In certain embodiments, an additive which prevents target modification is applied to the sample, prior to, during, or after the application of the electron transfer reagent, but before the irradiation of the sample. In some embodiments, signal modification may include a change in one or more signal characteristics, for example, a decrease in intensity of signal, a shift in the signal peak, or a change in the resonant frequency. In some embodiments, a photoreaction may modify the signal by substantially inactivating, i.e., bleaching, the fluorescent signal generator and the enzyme (if employed).

In some embodiments, an electron transfer reagent and the additive which prevents target modification may be in the form of a solution. In one embodiment, the electron transfer reagent and the additive which prevents target modification are present in the form of a buffered aqueous solution.

In some embodiments, the electron transfer reagent may be a borate salt. In further embodiments, the electron transfer reagent may be a lithium salt of a triphenyl butyl borate present at a concentration of 0.001 mM to 1000 mM. In a preferred embodiment, the concentration of borate is from 20 mM to 100 mM. In some embodiments, the concentration of the electron transfer reagent, e.g., borate salt, may represent 1-60 equivalents of the concentration of the signal generator, e.g., fluorescent dye.

In some embodiments, the additive which prevents target modification may be an antioxidants or free radical scavengers. In further embodiments, the antioxidants or free radical scavengers may be Ascorbic acid, n-propyl gallate, mercaptoethanol, cysteine hydrochloride, t-butyl hydroxy toluene (BHT), Cycloheptatriene (CHT), dioctyl phthalate (DOP), 1,4-Dihydro-o-toluamide (TA), a-tocopherol and trolox. In some embodiments, the additive which prevents target modification may be a singlet oxygen quencher. In further embodiments, the singlet oxygen quencher is a-tocopherol, ascorbic acid, curcurmin or DABCO.

In certain embodiments, the concentration of the scavenger is lower than the concentration of the electron transfer reagent. In certain preferred embodiments, the concentration of the scavenger is at least ten times lower than the concentration of the electron transfer reagent. In certain more preferred embodiments, the concentration of the scavenger is at least a hundred times lower than the concentration of the electron transfer reagent.

Irradiation of the sample contacted with the electron transfer reagent may be carried out for a predetermined amount of time. The duration of irradiation may depend on the desired duration of the photoreaction between the electron transfer reagent and the photoexcited signal generator. In some embodiments, the irradiation step may be performed for about 1 millisecond to about 60 minutes, preferably for about 100 milliseconds to about 15 minutes, and even more preferably, for about 1 second to about 5 minutes. In some embodiments, the irradiation step may be performed until no residual signal is observed from the signal generator. In some embodiments, the irradiation step may be performed at room temperature.

In some embodiments, the photoreaction is carried out at a temperature of 4-50° C., more preferably, at a temperature of 20-30° C.

In some embodiments, the photoreaction is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

In some embodiments, the conditions tor a photoreaction (e.g., irradiation wavelength) may be selected such that the binder, the target, the biological sample, and binding between the binder and the target may not be affected by the photoreaction. In some embodiments, the photoreaction may only affect the signal generator and the enzyme (if employed) and the electron transfer reagent, and may not affect the target/binder binding or the binder integrity. Thus, by way of example, a binder may include a primary antibody or a primary antibody/secondary combination. A photoreaction according to the methods disclosed herein may only affect the signal generator, and the primary antibody or primary antibody/secondary antibody combination may essentially remain unaffected. In some embodiments, a binder (such as, a primary antibody or primary antibody/ secondary antibody combination) may remain bound to the target in the biological sample after contacting the sample with the electron transfer reagent and the optional additive which prevents target modification and subsequent irradiation to initiate a photoreaction.

In some embodiments, after irradiating the sample, the sample is washed with a wash solution to remove residual electron transfer reagents from the sample. In certain embodiments, the sample is washed with a PBS solution. Effective removal of residual borate is important as residual borate in the sample can affect signal from subsequent staining. Amount of residual borate after PBS washes depends upon the borate salt used. High water solubility borate salts are substantially removed by PBS wash alone. In other cases PBS alone is insufficient to remove a significant amount of borate salt. In such cases an enabler may be added to PBS or used prior to PBS wash. In such embodiments, the sample is washed with a wash solution containing an enabler that effectively removes residual electron transfer reagents from the sample, in place of or followed by washing with a PBS solution. In some embodiments these enablers include organic solvent, cationic reagents, chaotropes, detergents or a combination thereof. In certain preferred embodiments, the enabler is ethanol.

In some embodiments, a characteristic of the signal may be detected after the photoreaction to determine the effectiveness of the signal modification. For example, a color may be observed before the photoreaction and the color may be absent after the photoreaction. In another example, fluorescence intensity from a fluorescent signal generator may be observed before the photoreaction and after the photoreaction. In some embodiments, a decrease in signal intensity by a predetermined amount may be referred to as signal modification, or photoactivated chemical bleaching, or bleaching. In some embodiments, modification of the signal, or photoactivated chemical bleaching, may refer to a decrease in the signal intensity by an amount in a range of greater than about 50 percent. In some embodiments, modification of the signal, or photoactivated chemical bleaching, may refer to a decrease in the signal intensity by an amount in a range of greater than about 60 percent. In some embodiments, modification of the signal, or photoactivated chemical bleaching, may refer to a decrease in the signal intensity by an amount in a range of greater than about 80 percent. In some embodiments, modification of the signal, or photoactivated chemical bleaching, may refer to a decrease in the signal intensity by an amount in a range of greater than about 90 percent. In some embodiments, modification of the signal, or photoactivated chemical bleaching, may refer to a decrease in the signal intensity by an amount in a range of greater than about 95 percent. In some embodiments, modification of the signal, or photoactivated chemical bleaching, may refer to a decrease in the signal intensity by an amount in a range of about 100 percent, or to complete bleaching.

Contacting the Sample with a Subsequent Probe and Binding to a Subsequent Target The biological sample or the sample may be contacted with a subsequent probe using one or more procedures described herein above for the first probe. The subsequent probe may be capable of binding to target different from the target bound in the earlier steps. In embodiments where a plurality of probes may be contacted with the biological sample in the earlier probe contact steps, the subsequent probe may be capable of binding a target different from the targets bound by the earlier probe set. In some embodiments, a biological sample may be contacted with a plurality of probes in the subsequent probe contact step. In some embodiments, where a plurality of multiple sets of probes was applied to a biological sample in the first step, a subsequent set of signals from the subsequent set of probes may be generated. Generation of the second set of signals may comprise associating the second set of probes with a separate moiety that comprises signal generator. For example, the second set of probes may comprise a biotin tag, and the moiety comprising signal generator may also comprise streptavidin capable of binding the biotin tag. Alternatively, generation of the second set of signals may comprise un-masking the signal-generating moiety, e.g., by modifying the distance between the fluorophore-quencher pair. In some embodiments generation of the second set of signals may be by hybridization of labeled probes complementary to sequences attached to the second set of probes.

In embodiments where binders coupled to enzymes may be employed as probes, binding steps may further include reacting steps involving reaction of the enzyme with an enzyme substrate coupled to fluorescent signal generator.

In some embodiments, the signal generator (e.g., a fluorescent signal generator) used in the different binding steps may be the same, that is, detectable in the same detection channel. Methods employing the same signal generator in different binding steps may allow for detection of multiple targets when limited number of detection channels are available. In some embodiments, where a set of probes (2 to 5 probes) may be employed in the first binding step, the subsequent probes may include the same signal generators as in the earlier binding steps. For example, a first binding step may include Cy3, Cy5, and Cy7-conjugated different binders. In some embodiments, the subsequent binding steps may also include the same dye set, that is, Cy3, Cy5, and Cy7.

In some embodiments, the signal generator (e.g., a fluorescent signal generator) used in the different binding steps may be different, that is, independently detectable in different detection channels. For example, in some embodiments, a first probe may include a Cy3 dye, which has a fluorescent emission wavelength in the green region and a subsequent probe may include a Cy7 dye, which has a fluorescent emission wavelength in the near infrared region.

In embodiments employing binder-coupled enzymes as probes, the enzymes and the substrates employed in the different binding and reacting steps may be the same. An earlier enzyme may be inactivated in the course of a photoreaction or in a separate inactivation step before binding the sample to a subsequent enzyme to prevent cross-reaction of the earlier enzyme with the subsequent substrate. For example, a first binding and reacting step may include binder coupled to HRP and tyramine coupled to a first fluorophore. The photoinduced chemical bleaching step may involve the steps of substantially inactivating the fluorophore and substantially inactivating the HRP. In some embodiments, photoinduced chemical bleaching and inactivation steps may occur simultaneously. In some embodiments, photoinduced chemical bleaching and inactivation steps may occur sequentially. In preferred embodiments, the photoinduced chemical bleaching is performed in the presence of an additive which prevents target modification. After the photoinduced chemical bleaching and inactivation steps, the sample may be contacted with a subsequent binder coupled to HRP, which may be further reacted with tyramine coupled to a second fluorophore. Similarly, the subsequent binding and reacting steps may be affected using multiple iterations of HRP-tyramine as enzyme substrate conjugates, each binding and reacting step followed by the photoinduced chemical bleaching and inactivation step. The first fluorophore and the subsequent fluorophores may be the same or different depending on the number of detection channels available for detection.

In some embodiments, the first binding step may include a set of probes (e.g., 2 to 5 probes), each probe including a binder capable of binding to a different target and each enzyme capable of catalyzing a chemical reaction of a different substrate. For example, in one embodiment, the first probe set may include a binder1 coupled to HRP and a binder2 coupled to AP. The reacting step may include contacting the sample with tyramine-coupled to Cy3 and NADP-coupled to Cy7. Following reaction of the enzymes with their corresponding substrates and observing the signals, the cyanine dyes may be inactivated by photoinduced chemical bleaching. In the optional presence of an additive which prevents target modification, and the enzymes inactivated in the course of a photoreaction or by addition of a suitable inactivating agent. The subsequent probing steps may include the same set of binder-enzyme and substrate-fluorophore pairs or different set of binder-enzyme and substrate-fluorophore pairs. The plurality of probes and the substrate-signal generator may be contacted with the biological sample simultaneously (for example, as a single mixture) or sequentially (for example, a probe1 may be contacted with the biological sample, followed by washing step to remove any unbound probe, followed by contacting a probe2 with the biological sample, and so forth).

Detecting a Subsequent Signal from a Subsequent Probe

One or more detection methods described hereinabove may be used to observe one or more characteristics of a subsequent (e.g., second, third, etc) signal from a subsequent signal generator (present in the subsequent probe). In some embodiments, signal intensity, signal wavelength, signal location, signal frequency, or signal shift may be determined using one or more of the aforementioned techniques. Similar to the first signal, a subsequent signal, (for example, a fluorescence signal) obtained may be recorded in the form of a digital signal (for example, a digitalized image). In some embodiments, defecting a subsequent signal may also include capturing an optical image of the biological sample.

Reiteration of the Contacting, Binding, and Detecting Steps

In some embodiments, after contacting the sample with a subsequent (e.g., second, third, etc.) probe, bleaching of the signal generator in a photoreaction, and subsequent probe administration/signal generation from already bound probes may be repeated multiple times. In some embodiments, after detecting a second signal from the second probe, the biological sample may be contacted with an electron transfer reagent and irradiated to modify the signal from the second probe. Optionally, the contacting and irradiating step is performed in the presence of an additive which prevents target modification. Furthermore, a third probe may be contacted with the biological sample, wherein the third probe may be capable of binding a target different from the first and the second probes. Likewise, a signal from the third probe may be detected and followed by application of electron transfer reagent and irradiation to modify the signal, performed optionally in the presence of an additive which prevents target modification. The binding, detecting, and bleaching steps may be repeated iteratively multiple times using an $n^{th}$ probe capable of binding to additional targets to provide the user with information about a variety of targets using a variety of probes and/or signal generators. In embodiments where binders coupled to enzymes may be employed as probes, binding steps may further include reacting steps involving reaction of the enzyme with an enzyme substrate coupled to fluorescent signal generator.

In some embodiments, the bleaching, binding, reacting (if applicable), and detecting steps may be repeated one or more time. In some embodiments, the bleaching, binding, reacting (if applicable), and detecting steps may be repeated at least 5, at least 15, at least 30, at least 60 times, at least 100 times, or at least 150 times. In some embodiments, the series of steps may be repeated 25-30 times. In other embodiments, the series of steps may be repeated 2-10 times.

In some embodiments, a series of probes may be contacted with the biological sample in a sequential manner to obtain a multiplexed analysis of the biological sample. In some embodiments, a series of probe sets (including at most 5 probes in one set) may be contacted with the biological sample in a sequential manner to obtain a multiplexed analysis of the biological sample. Multiplexed analysis generally refers to analysis of multiple targets in a biological sample using the same detection mechanism.

In some embodiments, where a biological sample is contacted with a plurality of multiple sets of probes in the first step, a series of steps comprising bleaching, generating signals front a subsequent set of probes and detecting the signal may be repeated at least 5, at least 15, at least 30, at least 60 times, at least 100 times, or at least 150 times. In some embodiments, the series of steps may be repeated 25-30 times. In other embodiments, the series of steps may be repeated 2-10 times.

In some embodiments, the components of a biological sample are not significantly modified after repeated cycles of the bleaching, binding, reacting (if applicable), and signal detecting steps. In some embodiments, the components of a biological sample are not significantly modified during the bleaching step. In some embodiments, the components of the biological sample that are not significantly modified during the bleaching step are targets. In some embodiment, more than 80% of targets are not significantly modified in the coarse of the bleaching step. In some embodiments, more than 95% of targets are not significantly modified in the coarse of the bleaching step.

Contacting the Sample with One or More Morphological Stain

In some embodiments, a biological sample may include a cell or a tissue, and the sample may be contacted with a morphological stain before, during, or after the contacting step with the first probe or subsequent probe. A morphological stain may include a dye that may stain different cellular components, in order to facilitate identification of cell type or disease status. In some embodiments, the morphological stain may be readily distinguishable from the signal generators in the probes, that is, the stain may not emit signal that may overlap with signal from the probe. For example, for a fluorescent morphological stain, the signal from the morphological stain may not autofluoresce in the same wavelength as the fluorophores used in the probes.

A morphological stain may be contacted with the biological sample before, during, or after, any one of the aforementioned steps. In some embodiments, a morphological stain may be contacted with biological sample along with the first probe contact step. In some embodiments, a morphological stain may be contacted with the biological sample before contacting the sample with an electron transfer reagent and an optional additive which prevents target modification and irradiated after binding the first probe to the target. In some embodiments, a morphological stain may be contacted with a biological sample after contacting the sample with an electron transfer reagent and an optional additive which prevents target modification and irradiation to modify the signal. In some embodiments, a morphological stain may be contacted with a biological sample along with the second probe contact step. In some embodiments, a biological sample may be contacted with the morphological stain after binding the second probe to the target. In some embodiments, where the morphological stains may result in background noise for the fluorescent signal from the signal generator, the morphological stains may be contacted with the biological sample after the probing, bleaching and reprobing steps. For example, morphological stains like H&E may be sequentially imaged and registered after the methods disclosed herein.

In some embodiments, chromophores, fluorophores, or enzyme/enzyme substrates may be used as morphological stains. Suitable examples of chromophores that may be used as morphological stains (and their target cells, subcellular compartments, or cellular components) may include, but are not limited to, Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments). Methyl Green (amyloid), pyronin (nucleic acids), Naphthol Yellow (red blood cells), Neutral Red (nuclei), Papanicolaou stain (a mixture of Hematoxylin, Orange G and Bismarck Brown mixture (overall cell morphology)), Red Counterstain B (Trevigen), Red Counterstain C (Trevigen), Sirius Red (amyloid), Feulgen reagent (pararosanilin) (DNA), Gallocyanin chrom-alum (DNA). Gallocyanin chrom-alum and Naphthol Yellow S (DNA), Methyl Green-Pyronin Y (DNA). Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and light Green mixture) (stains collagen, cytoplasm, nucleioli differently), Aldehyde Fuchsin (elastin fibers), or Weigert stain (differentiates reticular and collagenous fibers).

Examples of suitable fluorescent morphological stains (and their target cells, subcellular compartments, or cellular components if applicable) may include, but are not limited to: 4',6-diamidino-2-phenylindole (DAPI) (nucleic acids), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids). Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

Examples of suitable enzymes (and their primary cellular locations or activities) may include, but are not limited to, ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), acid phosphatases (lysosomes), leucine aminopeptidases (liver cells), dehydrogenases (mitochondria), myodenylate deaminases (muscle cells), NAPH diaphorases (erythrocytes), and sucrases (small intestine).

In some embodiments, a morphological stain may be stable towards photoactivated chemical bleaching, that is, the signal generating properties of the morphological stain may not be substantially affected by a photoreaction comprising contacting the morphological stain with an electron transfer reagent and an optional additive which prevents target modification and subsequent irradiation. In some embodiments, where a biological sample may be stained with a probe and a morphological stain at the same time, a bleaching of the signal from the probe may not modify the signal from the morphological stain. In some embodiments, a morphological stain may be used as a control to co-register the molecular information (obtained through the iterative probing steps) and the morphological information (obtained through the morphological stains). In some embodiments, the morphological stain is not modified by the electron transfer reagent and the additive which prevents target modification upon irradiation of the sample.

Contacting the Sample with One or More Control Probe

In some embodiments, a control probe may be bonded to one or more targets in the biological sample. In some embodiments, a control probe may be bonded to the targets along with the first probe contact step. In some embodiments, a control probe may be applied to the biological sample simultaneously with the first probe. In some embodiments, a control probe may be applied to the biological sample sequentially, that is before or after the application of the first probe, but before application of the electron transfer reagent and the optional additive which prevents target modification and subsequent irradiation.

A control probe may include a signal generator that is stable towards photoactivated chemical bleaching or the signal generating properties of the signal generator are not substantially affected when contacted with the electron transfer reagent and the optional additive which prevents target modification and subsequent irradiation. A signal generator may include a radioisotope that is stable during exposure to an electron transfer reagent and the additive which prevents target modification and irradiation or a fluorophore that is not chemically modified upon exposure to an electron transfer reagent and the additive which prevents target modification and irradiation. A suitable radioisotope may include $P^{32}$, $^3H$, $^{14}C$, $^{125}I$ or $^{131}I$. A suitable flourophore may include DAPI.

In some embodiments, a suitable signal generator may be coupled to a binder to form a control probe. For example, a radioactive label may be coupled to an antibody to form a control probe and the antibody may bind to one or more target antigens present in the biological sample. In other embodiments, a suitable signal generator may be capable of binding to one or more targets in the sample and also providing a detectable signal, which is stable in the presence of the electron transfer reagent and the optional additive which prevents target modification and during irradiation. For example, a suitable control probe may be DAPI, which is capable of binding to nucleic acids in the sample and also capable of providing a fluorescent signal that is substantially stable to photoactivated chemical bleaching, i.e., that is not substantially modified after addition of an electron transfer reagent and the additive which prevents target modification and subsequent irradiation.

In some embodiments, a control probe may be employed in the methods disclosed herein to provide an indication of the stability of the targets to the iterative staining steps. For example, a control probe may be bonded to a known target in the sample and a signal from the control observed and quantified. The control signal may be then monitored during the iterative staining steps to provide an indication of the stability of the targets or binders to the electron transfer reagent, the optional additive which prevents target modification, and subsequent irradiation. In some embodiments, a quantitative measure (for example, signal intensity) of the control signal may be monitored to quantify the amount of targets present in the sample after the iterative probing steps.

In some embodiments, a control probe may be employed to obtain quantitative information of the sample of interest, for example concentration of targets in the sample or molecular weight of the targets in the sample. For example, a control target (having known concentration or known molecular weight) may be loaded along with the sample of interest in a blotting technique. A control probe may be bonded to the control target and a control signal observed.

The control signal may be then correlated with the signals observed from the sample of interest using methods described herein below.

In some embodiments, a control probe may be employed in the methods disclosed herein to provide for co-registration of multiple molecular information (obtained through the iterative probing steps) and the morphological information (obtained, e.g., using DAPI). In some embodiments, methods disclosed herein may include co-registration of multiple fluorescent images with the bright-field morphological images obtained e.g., using H&E. In some embodiments, the probes employed in the iterative probing steps may not have any common compartmental information that may be used to register with the H&E images. A control probe like a DAPI nuclear stain may be employed to co-register the nucleus stained with hematoxylin in the bright-field images with the fluorescent images. The fluorescent images and the bright-field images may be co-registered using image registration algorithms that may be grouped in two categories: intensity-based and feature-based techniques.

Correlating the First Signal and the Subsequent Signals

In some embodiments, a first signal, a subsequent signal, or the first signal and the subsequent signals may be analyzed to obtain information regarding the biological sample. For example, in some embodiments, a presence or absence of a first signal may indicate the presence or absence of the first target (capable of binding to the first binder) in the biological sample. Similarly, the presence or absence of a second signal may indicate the presence or absence of the second target (capable of binding to the second binder in the biological sample), In embodiments where multiple targets may be analyzed using a plurality of probes, the presence or absence of a particular signal may indicate the presence or absence of corresponding target in the biological sample.

In some embodiments, the observing steps may include a quantitative measurement of at least one target to the sample. In some embodiments, an intensity value of a signal (for example, fluorescence intensity) may be measured and may be correlated to the amount of target in the biological sample. A correlation between the amount of target and the signal intensity may be determined using calibration standards. In some embodiment, intensity values of the first and second signals may be measured and correlated to the respective target amounts. In some embodiments, by comparing the two signal intensities, the relative amounts of the first target and the second target (with respect to each other or with respect to a control) may be ascertained. Similarly, where multiple targets may be analyzed using multiple probes, relative amounts of different targets in the biological sample may be determined by measuring different signal intensities. In some embodiments, one or more control samples may be used as described hereinabove. By observing a presence or absence of a signal in the samples (biological sample of interest versus a control), information regarding the biological sample may be obtained. For example by comparing a diseased tissue sample versus a normal tissue sample, information regarding the targets present in the diseased tissue sample may be obtained. Similarly by comparing signal intensities between the samples (i.e., sample of interest and one or more control), information regarding the expression of targets in the sample may be obtained.

In some embodiments, the detecting steps include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel images of a Tissue Micro Array", filed on Aug. 7, 2006; U.S. patent application Ser. No. 11/606,582, entitled "System, and Methods for Scoring Images of a Tissue Micro Array", filed on Nov. 30, 2006, and U.S. Pat. No. 8,036,462, entitled Automated Segmentation of Image Structures, each of which is herein incorporated by reference.

In some embodiments, a location of the signal in the biological sample may be detected. In some embodiments, a localization of the signal in the biological signal may be detected using morphological stains. In some embodiments relative locations of two or more signals may be observed. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

In embodiments employing blotting techniques, the detecting steps may include detecting a location of the signal on the blot. The location of the signal in the blot may be then correlated with calibration standards loaded along with the sample in the gel to obtain information regarding the molecular weight of the targets in the different bands. In some embodiments, a location of the signal on the blot may be correlated to a molecular weight of the target and the isoelectric point of the target, e.g., in 2D-PAGE. In some embodiments, structural proteins such as actin or tubulin may be probed using control probes in western blots to quantify the amount of targets in the sample.

In some embodiments, one or more of the detecting or correlating step may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In some embodiments, one or more of the aforementioned methods may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

EXAMPLES

The following examples are intended only to illustrate methods and embodiments in accordance with the invention, and as such should not be construed as imposing limitations upon the claims.

Example 1. Photoactivated Chemical Bleaching of Cyanine Dyes: Dose Response

To a solution of Cy3 in PBS, 2-60 equivalents of triphenylbutyl borate lithium salt were added, and the solution was irradiated for 4 minutes or for 10 minutes. Absorbance at 550 nm was measured to monitor photoactivated chemical bleaching, and the results were plotted, as is shown in FIG. 1. The solid line with squares represents A550 absorbance after Gy3 dye was irradiated for 4 minutes in the presence of different concentrations of triphenylbutyl borate. The solid line with diamonds represents A550 absorbance after Cy3 dye was irradiated for 10 minutes in the presence of different concentrations of triphenylbutyl borate. The results demonstrate that the extent of Cy3 bleaching increases with increasing concentration of the borate salt.

Example 2. Comparison of Cy3 Bleaching by Photoreaction and Thermal Oxidation

Three methods for bleaching Cy3 were compared. For the photoactivated chemical bleaching reaction, Cy3 was mixed with triphenylbutylborate lithium salt and irradiated for 20 seconds. For the thermal oxidation reaction, Cy3 was mixed with basic hydrogen peroxide and incubated for 20 seconds. For the control reaction, Cy3 was incubated with water for 20 seconds. The color of the Cy3 solution in all three reactions was compared before and after each incubation and/or reaction. The control reaction does not change its dark pink color. The color of the thermal oxidation reaction changes front dark pink to light pink after 20 seconds of thermal oxidation. The photoactivated chemical bleaching reaction turns from dark pink to colorless after 20 seconds of irradiation.

Example 3. Photoactivated Chemical Bleaching of Cy3 and Cy5 in Tissues

Tissue Microarrays (TMA, Pantomics Catalog No. MTU541C) were stained with Cy3-conjugated cytokeratin and Cy5-conjugated pan-cadherin. Photoactivated chemical bleaching of the Cy3 and Cy5 was accomplished by incubating stained TMAs with tripbenylbutylborate lithium salt and irradiation for 2 minutes. Images were taken on the Olympus Microscope before and after bleaching. Images of samples stained with Cy3-conjugated cytokeratin before and after bleaching are shown in FIG. 2. Images of samples stained with Cy5-conjugated pan-cadherin before and after bleaching are shown in FIG. 3. This data demonstrates that photoactivated chemical bleaching effectively destroys Cy3 and Cy5 signals in stained tissues.

Example 4. Photoactivated Chemical Bleaching of BODIPY

Figure 4:
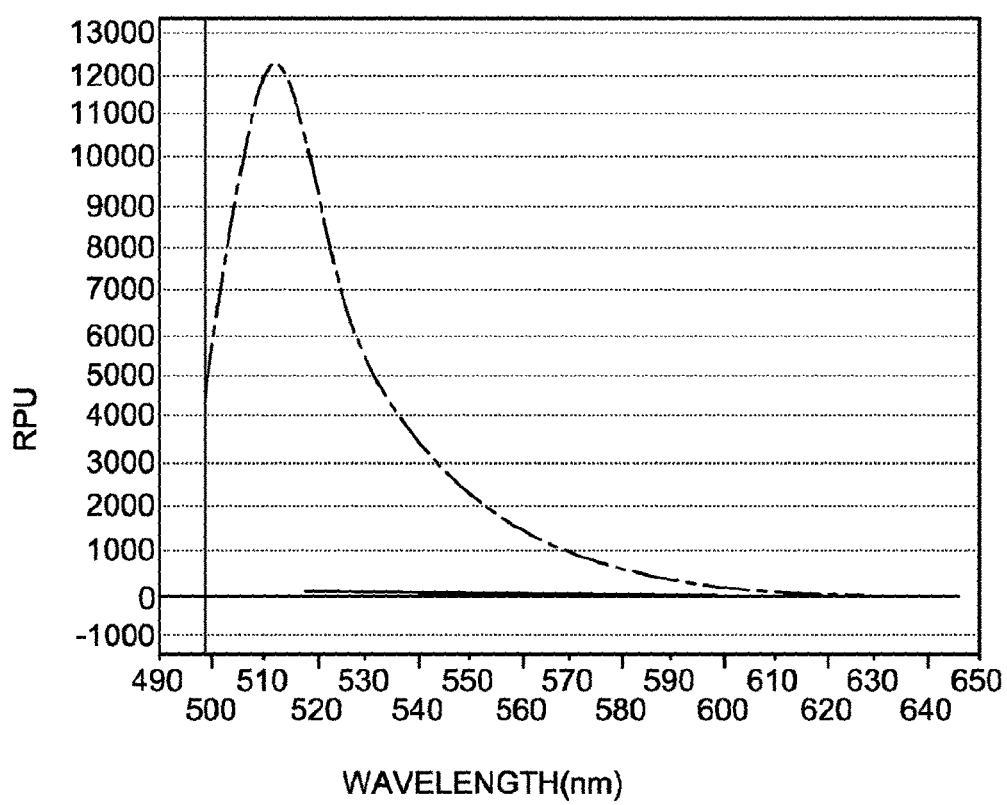
FIG. 4 shows a grayscale image of fluorescence spectrum of BODIPY dye before and after photoactivated chemical bleaching.

The photoactivated chemical bleaching reaction of BODIPY was carried out in methanol/water without or with 100 mM solution of triphenylbutyl borate lithium salt. Irradiation of both samples was carried out for 2 minutes using 100 W halogen lamp. The bright yellow color of the reaction vial including BODIPY and triphenylbutyl borate salt becomes pale yellowish after irradiation. Shown in FIG. 4 is the fluorescence spectrum of the reaction before irradiation (unevenly broken line) and after irradiation (solid line). The fluorescence spectrum demonstrates complete fluorescence quenching of BODIPY by photoactivated chemical bleaching. The bright yellow color of the reaction vial including BODIPY without triphenylbutyl borate salt maintains its bright yellow color after irradiation.

Example 5. Photoactivated Chemical Bleaching of Rhodamine

Figure 5:
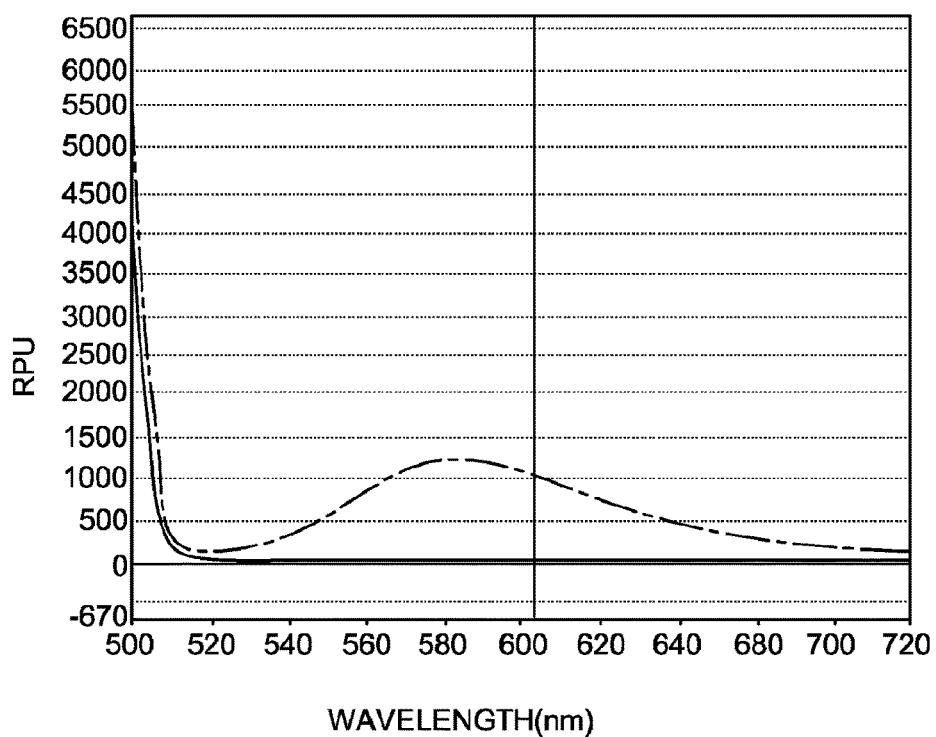
FIG. 5 shows a grayscale image of a fluorescence spectrum of rhodamine dye before and after photoactivated chemical bleaching.

The photoactivated chemical bleaching reaction of rhodamine was carried out in Methanol/water without or with 100 mM solution of tripbenylbutylborate lithium salt. Irradiation of both samples was carried out for 2 minutes using 100 W halogen lamp. The bright red color of the reaction vial including rhodamine and triphenylbutylborate lithium salt is lost after irradiation. Shown in FIG. 5 is the fluorescence spectrum of the reaction before irradiation (unevenly broken line) and after irradiation (solid line). The fluorescence spectrum demonstrates complete fluorescence quenching of rhodamine by photoactivated chemical bleaching. The bright red color of the reaction vial including rhodamine without triphenylbutyl borate salt maintains its bright red color after irradiation.

Example 6. Photoactivated Chemical Bleaching of 1,3-Dichloro-7-Hydroxy-9,9-Dimethyl-2(9H)-Acridinone (DDAO)

Figure 6:
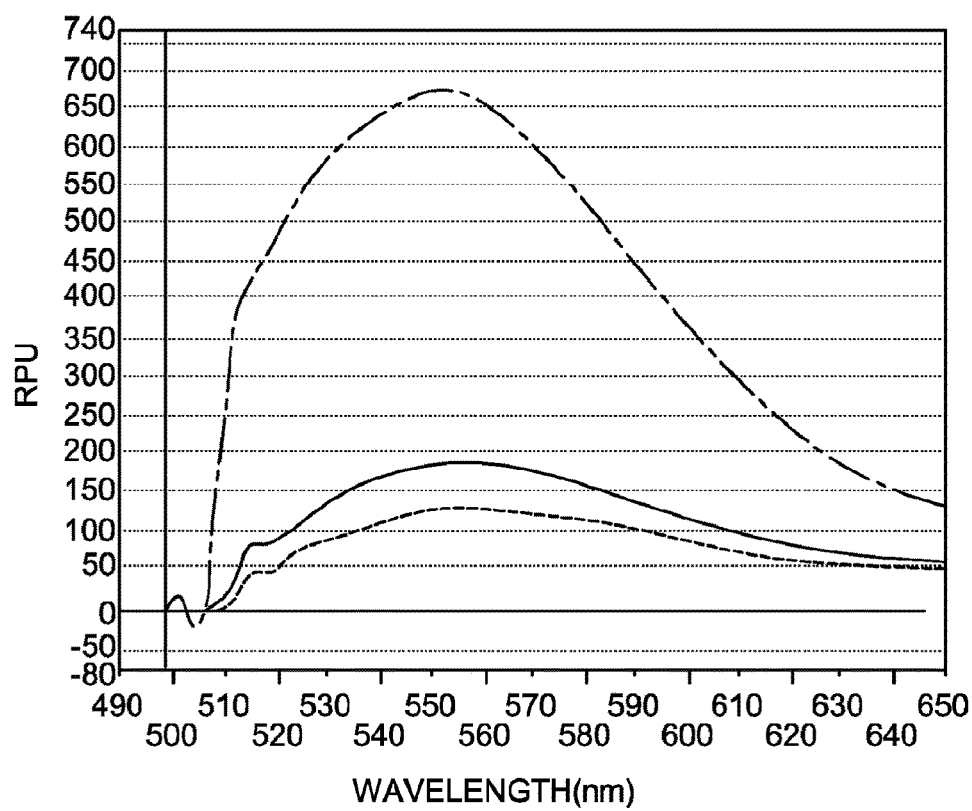
FIG. 6 shows a grayscale image of a fluorescence spectrum of 1,3-dichloro-7-hydroxy-9,9-dimethyl-2(9H)-Acridinone (DDAO) dye before and after photoactivated chemical bleaching.

The photoactivated chemical bleaching reaction of acridone was carried out in methanol/water without or with 100 mM solution of triphenylbutylborate lithium salt. Irradiation of both samples was carried out for 2 minutes using 100 W halogen lamp. The brown color of the reaction becomes yellow after irradiation. Shown in FIG. 6 is the fluorescence spectrum of the reaction before irradiation (unevenly broken line), after 1 irradiation, (solid line) and after 2 minute irradiation (evenly broken line). The fluorescence spectrum also demonstrates incomplete fluorescence quenching of DDAO in the limited time used for irradiation. The brown color of the reaction vial including DDAO without triphenylbutyl borate salt maintains its brown color after irradiation.

Example 7. Use of Scavenger in Photoactivated Chemical Bleaching of Cy3

1. Preparation of Tissue Samples

Human lung tissue array samples were obtained as tissue slides embedded in paraffin. These samples included microarray of adeno, squamous, small cell and large cell lung carcinoma.

2. Slide Clearing

Three paraffin embedded slides were baked at 60° C. for one hour with tissue facing up and parallel to the oven rack. After baking, slides were deparaffinized by washing in xylene with gentle agitation for ten minutes. The samples were then rehydrated by washing in four solutions of ethanol with concentrations decreasing in the order of 100%, 95%, 70%, and 50% followed by a wash with 1× phosphate buffer saline (PBS, pH 7.4). After rehydration, the slides were washed with 1×PBS. A ten minute wash in 0.3% Triton X-100 in PBS was performed for membrane permeablization of the tissue, followed by a wash with 1×PBS.

3. Antigen Retrieval

After the slide clearing process, slides were treated with dual-buffer heat-induced epitope retrieval. Using a pressure cooker the slides were exposed to 70° C. Citrate Buffer pH 6.0 (Vector Unmasking Solution), heated to a temperature of 110° C. that was held for 4 minutes and reached a pressure of ~7 psi then gradually cooled (final temperature of 96° C.). Slides were in Citrate Buffer for a total of twenty minutes and then transferred to hot (96° C.) Tris-EDTA Buffer pH 9.0 and allowed to stand in the cooker at atmospheric pressure with gradual cooling for twenty minutes. This was followed by cooling down at room temperature for ten minutes and a series of washes in 1×PBS.

4. Blocking

Following antigen retrieval the slides were blocked against nonspecific binding by incubating overnight in a 10% donkey serum, 3% bovine serum albumin (BSA) solution at 4° C.

5. Stabling and Imaging

Slides were stained with DAPI and cover slipped. Images were taken at 20× prior to protein staining to baseline the auto fluorescence from Cy3 and Cy5 channels. Slides were decoverslipped in 1×PBS and stained with a cocktail of Cy3 and Cy5 direct conjugate diluted in 3% BSA in 1×PBS (Round 1) as shown in the table below. Incubation was for one hour at room temperature. After incubation, a series of washes in 1×PBS removed excess antibodies and slides were cover slipped. The samples were imaged and then decoverslipped. After decoverslipping each slide is bleached as described below with the conditions in the table.

Bleaching Protocol
- (a) Slide 1—is treated with butyl borate 10 mM prepared in PBS and irradiated the slide with visible lamps (photoactivated chemical bleaching)
- (b) Slide 2—treated with butyl borate (10 mM) and propyl gallate 100 uM prepared in PBS and irradiated the slide with visible lamps (photoactivated chemical bleaching)
- (e) Slide 3—treated with butyl borate (10 mM) and DABCO 10 uM prepared in PBS and irradiated the slide with visible lamps (photoactivated chemical bleaching)
- (d) Slide 4—heated with butyl borate (10 mM) and ascorbic acid 100 uM prepared in PBS and irradiated the slide with visible lamps (photoactivated chemical bleaching)
- (e) Slide 5—treated with NaHCO3 and H2O2 for 15 minutes (Thermal bleaching)

After bleaching all the slides were washed with PBS and coverslipped to acquire bleached background images. Slides were decoverslipped and next round of antibodies were applied as discussed in Staining and Imaging. Bleaching for subsequent steps is same as described in Bleaching Protocol

| | | photoactivated chemical bleaching | | | |
|---|---|---|---|---|---|
| Rounds | None (a) | (b) Propyl gallate 100 uM | (c) DABCO 10 uM | (d) Ascorbic acid | H2O2/ NaHCO3 Thermal bleaching |
| Round 1- PCK26-cy3 @ 2.5 ug/mL + Pcadherin-cy5 @ 5 ug/mL | Slide 1 | Slide 2 | Slide 3 | Slide 4 | Slide 5 |
| Round 2- Trim29-cy3 @ 10 ug/mL + CEACAM5-cy5 @ 5 ug/mL | Slide 1 | Slide 2 | Slide 3 | Slide 4 | Slide 5 |
| Round 3- MUC1-cy3 @ 1 ug/mL + SLC7A5 @ 5 ug/mL | Slide 1 | Slide 2 | Slide 3 | Slide 4 | Slide 5 |
| Round 4- NapsinA-cy3 @ 1 ug/mL + p63-cy5 @ 5 ug/mL | Slide 1 | Slide 2 | Slide 3 | Slide 4 | Slide 5 |
| Round 5- EGFR-Cy3 @ 10 ug/mL + pEGFR-Cy5 @ 10 ug/mL | Slide 1 | Slide 2 | Slide 3 | Slide 4 | Slide 5 |

6. Results and Discussion

Figure 7:
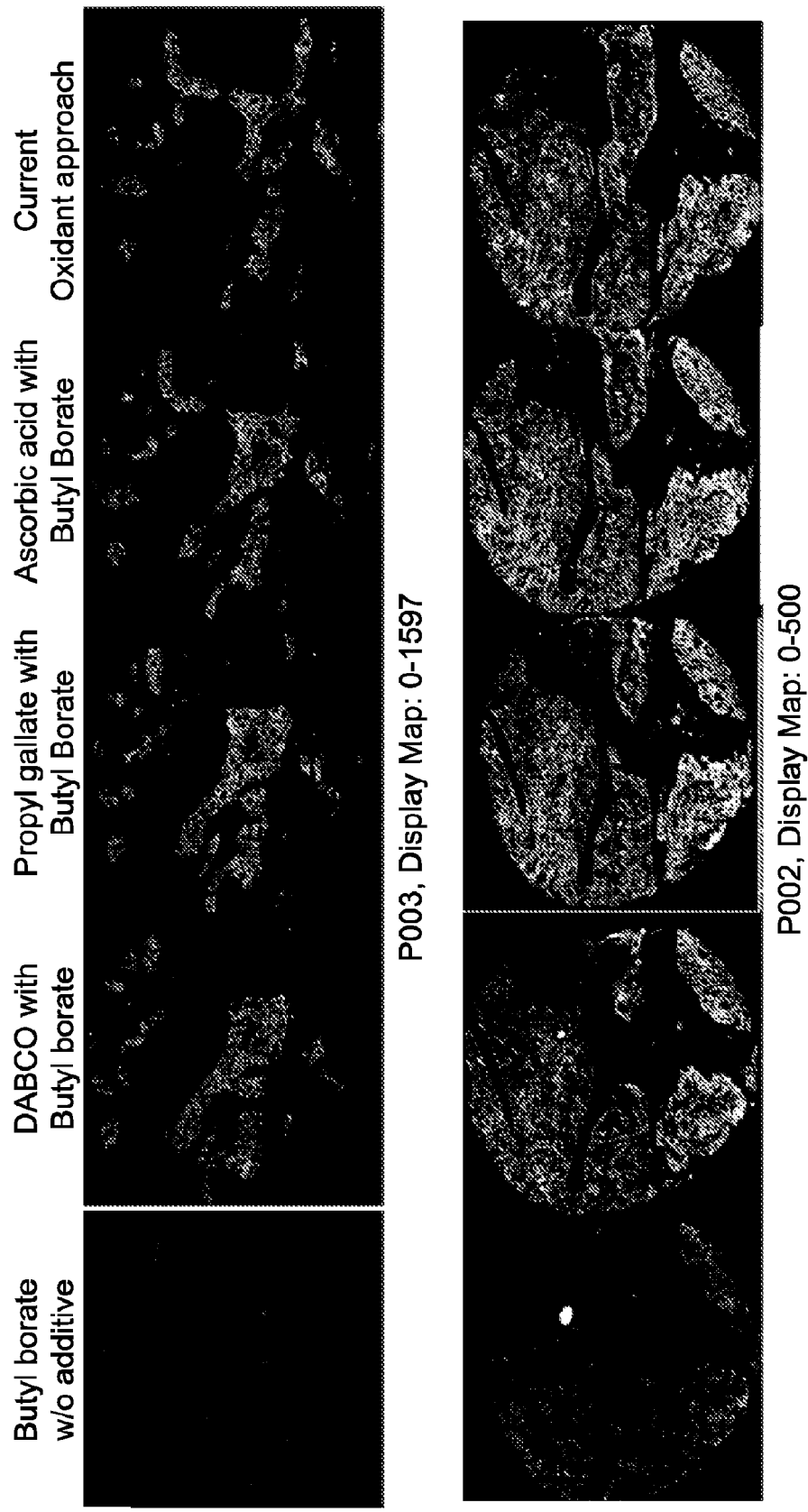
FIG. 7 shows a tissue microarray image of samples stained with fluorescently labeled TRIM29 antibody after the TMA was subjected to photo-induced electron transfer bleaching under various conditions listed and as discussed in the Examples Section. Quenchers are shown to prevent the TRIM29 epitope damage that results from bleaching by photo-induced electron transfer process.

Serial sections of a tissue microarray were stained with fluorescently labeled PCK26 antibody as discussed in Staining and Imaging. Each slide was then bleached by photoinduced electron transfer between the fluorescent dye and triphenylbutylborate in the presence or absence of a singlet oxygen and/or free radical quencher. One slide was bleached with basic hydrogen peroxide. Slides were then stained for TRIM29. Images for two tissue cores (P002 & P003) are shown above. Quenchers are shown to prevent the TRIM29 epitope damage that results from bleaching by photo-induced electron transfer process. (FIG. 7). When radical scavengers like DABCO, propyl gallate and ascorbic acid are employed, restaining with the subsequent TRIM29 biomarker looks as effectively stained as the slide that went through oxidant ($NaHCO_3/H_2O_2$) based bleaching.

Figure 8:
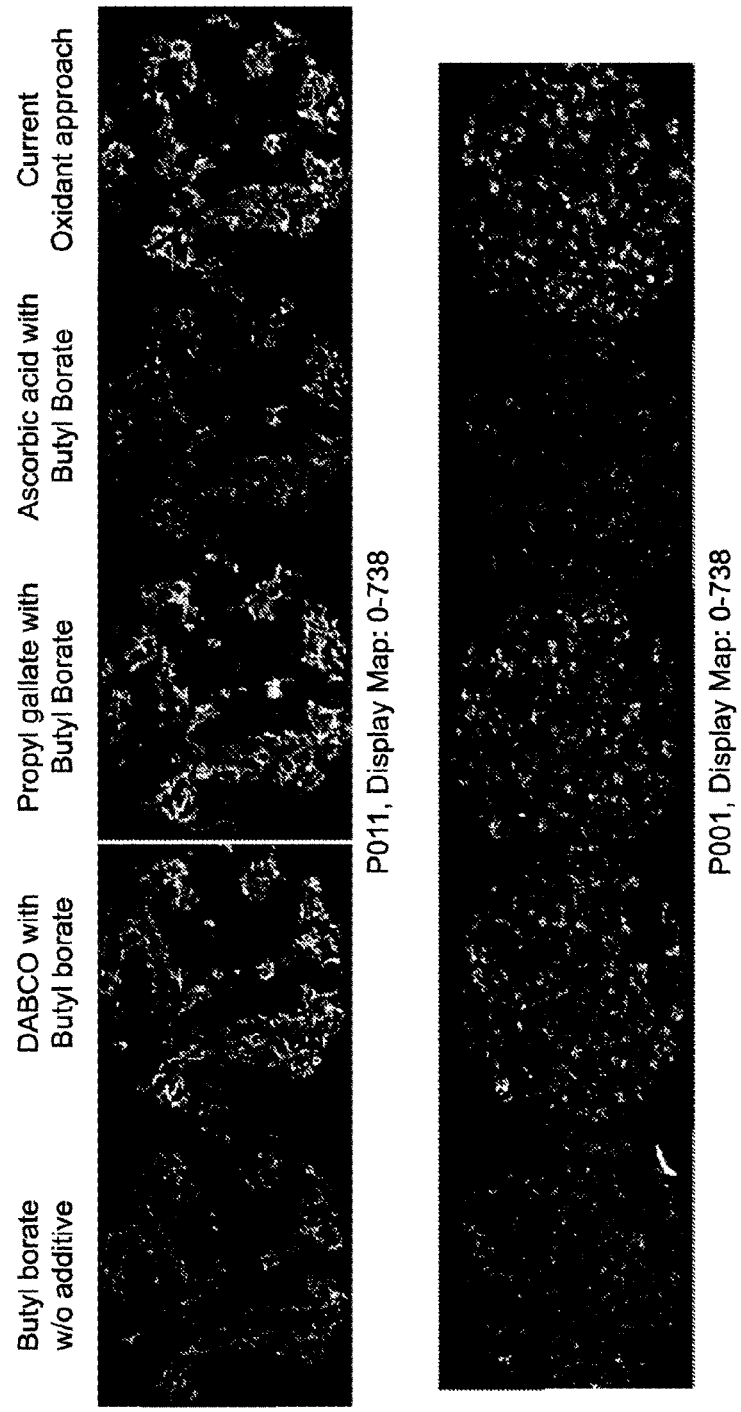
FIG. 8 shows a tissue microarray image of samples stained with fluorescently labeled MUC1 antibody as discussed in the Examples Section. Quenchers are shown to prevent the MUC1 epitope damage that results from bleaching by photo-induced electron transfer process.

After bleaching of the Cy3 signal from antibody for TRIM29, the slides were stained with Cy3 labeled antibody for MUC1, FIG. 8 shows the results, including the antigen effects (epitope damage) in the absence of radical scavengers when triarylbutylborate was used to bleach the previous Cy3 signal associated with the TRIM29 biomarker. When radical scavengers like DABCO, propyl gallate and ascorbic acid are employed the restaining with the subsequent MUC1 biomarker looks as effectively stained as the slide that went through oxidant ($NaHCO_3/H_2O_2$) based bleaching. DABCO & propyl gallate are shown to be more effective in preventing target modification compared to ascorbic acid.

Figure 9:
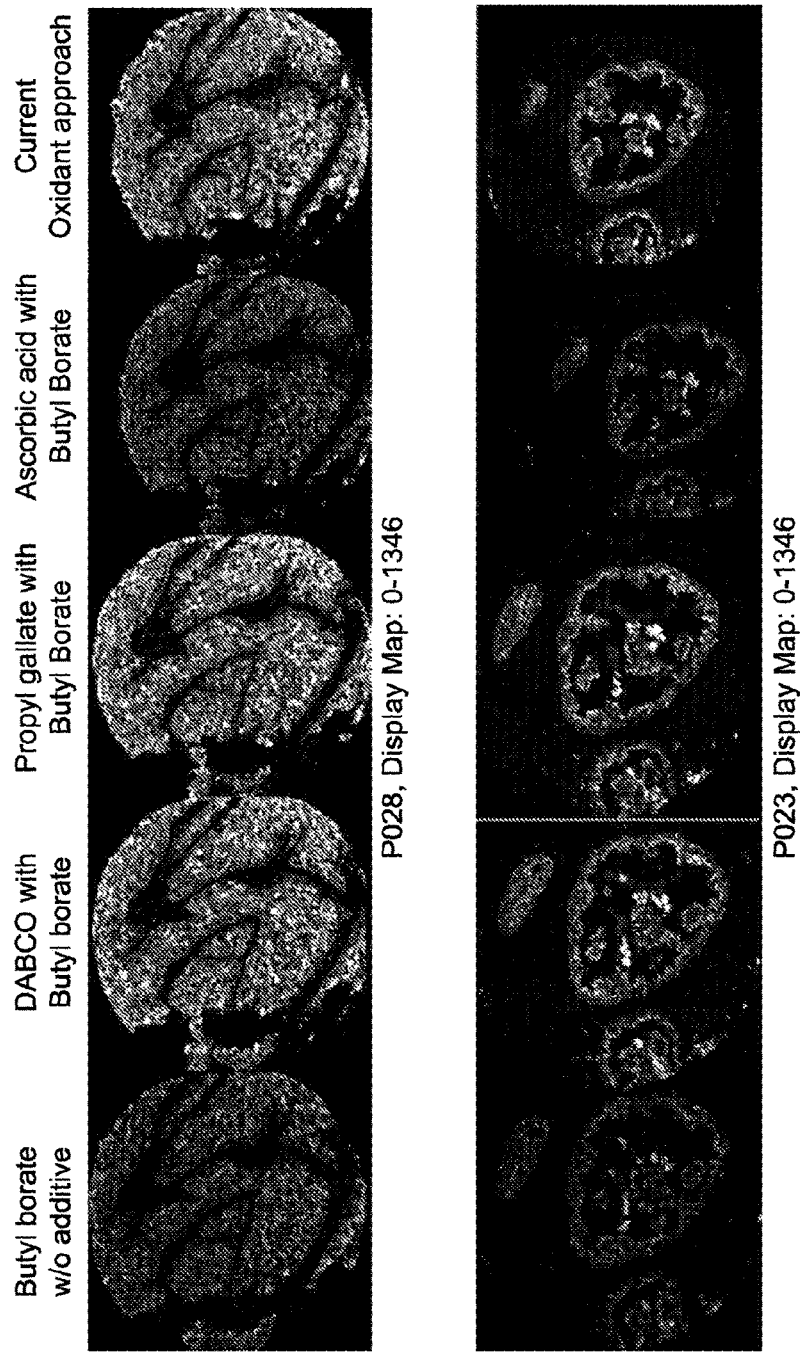
FIG. 9 shows a tissue microarray image of samples stained with fluorescently labeled Napsin A antibody as discussed in the Examples Section. Quenchers are shown to prevent the Napsin A epitope damage that results from bleaching by photo-induced electron transfer process.

After bleaching of the Cy3 signal from antibody for MUC1, the slides were stained with Cy3 labeled antibody for Napsin A. FIG. 9 shows the results, including the antigen effects (target modification) in the absence of radical scavenger when triarylbutylborate was used to bleach the previous Cy3 signal associated with the MUC1 biomarker. When radical scavengers like DABCO, propyl gallate and ascorbic acid are employed the restaining with the subsequent Napsin A biomarker looks as effectively stained as the slide that went through oxidant ($NaHCO_3/H_2O_2$) based bleaching.

Example 8. Removal of Residual Borate after Photoactivated Chemical Bleaching Cycle 1. Preparation of Tissue Samples Human multi tissue array samples were obtained as tissue slides embedded in paraffin. These samples included microarray of normal, premalignant, and cancer tissues with progressive grades (Pantomics, MNT241).
2. Slide Clearing (See Example 7)
3. Antigen Retrieval (See Example 7)
4. Blocking (See Example 7)

Figure 10:
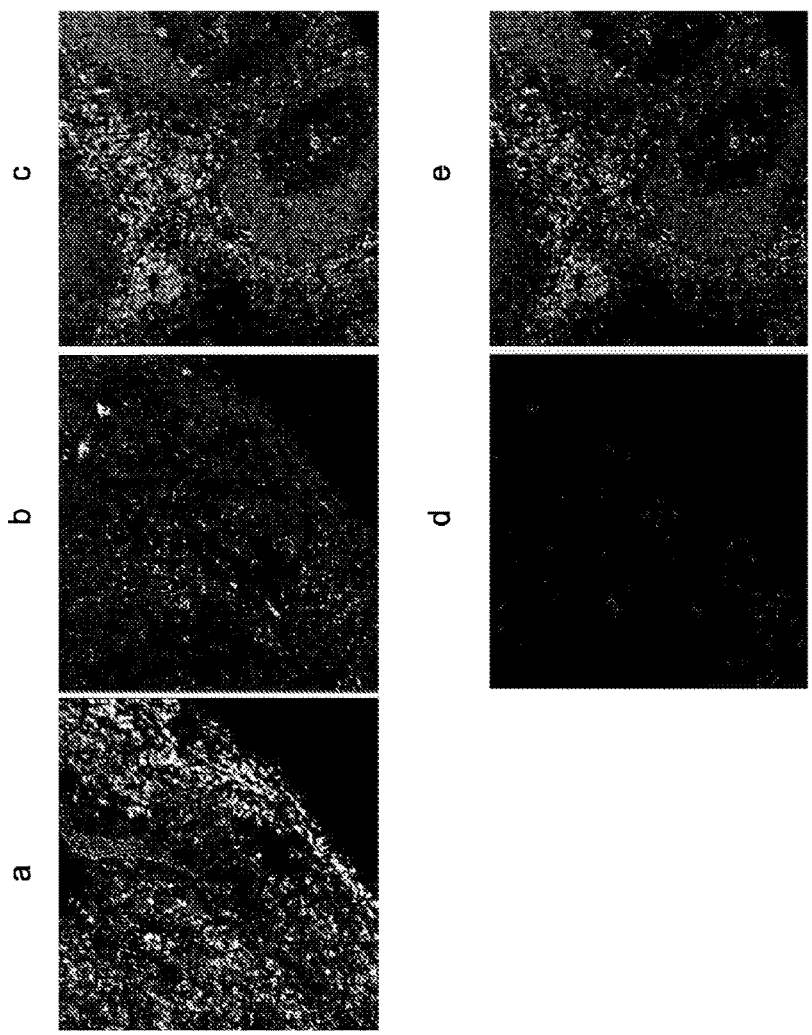
FIG. 10: Effect of residual borate on signal from subsequent staining and imaging and removal of residual borate with ethanol wash.

Experiment 1: Removal of Residual Borate from Tissue Retained During the Bleaching cycle Previously stained slides (stained with Cy5-labeled anti-S6 antibody) were bleached by exposure to visible light in the presence of 500 ul of monobenzyl triphenylborate (1 mM)/DABCO (100 uM) solution for 7 minutes. Slides were either washed with PBS 3× or 50% ethanol 3× followed by PBS 3×. Slides were imaged, exposed to light in the Cy5 channel on the microscope itself for 1 min and then reimaged. A separate slide which was bleached with basic peroxide, stained with anti-S6 antibody and washed with PBS 3× was used as a control. As shown in FIG. 10, slide previously bleached with photoinduced electron transfer process and only washed with PBS showed diminished signal, which was further reduced upon prolonged exposure. Signal from the slide that underwent additional ethanol washes wasn't dramatically affected.

FIG. 10: Effect of residual borate on signal front subsequent staining and imaging and removal of residual borate with ethanol, a) image of control slide bleached with basic peroxide, b) image of slide bleached with PICB, but washed with PBS alone, c) image of slide bleached with PICB and then washed with 50% ethanol prior to PBS washes, d) & e) images of b) & c) respectively after the slides were exposed to light in the Cy5 channel for 1 minute prior to reimaging.

Experiment 2: Evaluation of Other Reagents/Buffers to Remove Residual Borate

Experiment was conducted as described above for Experiment 1 except after bleaching with PICB, slides were washed with different reagents/buffers for 3×5 minutes prior to washes with PBS. Slides were stained with anti-NaKAT-Pase-Cy5 and anti-CD79-Cy3 or AE1-Cy3 antibody conjugates. Slides were imaged, exposed to light for 1 minute and then re-imaged as described above. A control slide was also used as described above for Experiment 1. Results are shown in FIG. 11.

FIG. 11(a) Evaluation of different reagents/buffers for removing residual borate as measured by subsequent effects on signal from next round of staining and prolonged light exposure, a) wash with 50% ethanol, b) wash with 0.1% polyethyleneimine, c) wash with commercial Leica Bond wash solution, d) wash with 0.1% Lysine, e) wash with commercial Biocare wash solution, f) wash with 0.1% CTAB and g) wash with 0.1% Guanidine. Different reagents are effective to different extent.

Figure 11B:
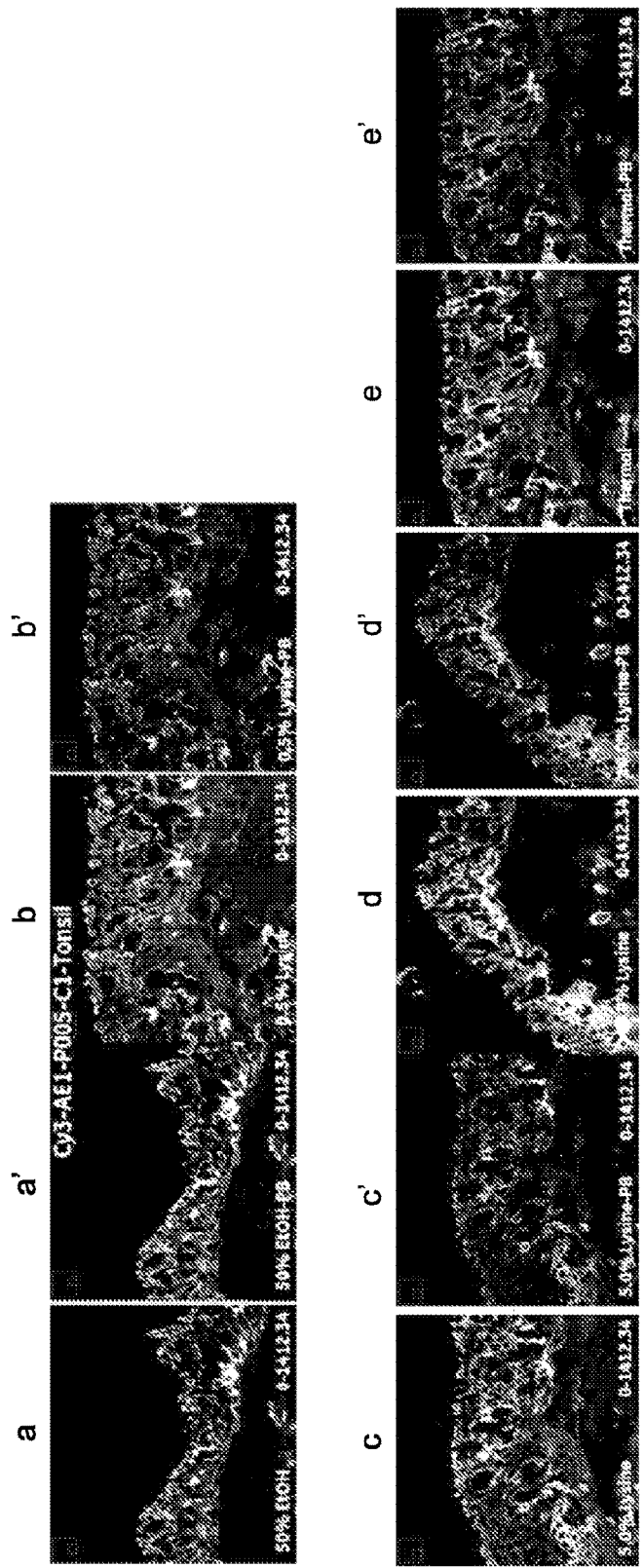
FIG. 11(b); Evaluation of various reagents/buffers for removing residual borate: Effect of reagent concentration.

FIG. 11(b): Evaluation of various reagents/buffers to remove residual borate: Effect of reagent concentration: a) image of slide washed with 50% ethanol, b) image of slide washed with 0.5% Lysine, c) image of slide washed with 5% lysine, d) image of slide washed with 10% lysine, e) image of control slide, a'-e') images of a-e after exposure to light for 1 minute. Higher concentration of lysine is more effective indicating that washing conditions can be further fine-tuned.

Experiment 3: Effect of Different Percentage of Ethanol on Residual Borate Removal Previously stained tissue microarray slides were bleached by PICB as described in Experiment 1 and then washed with different percentage of ethanol (3×5 min) followed by deionized water prior to subjecting slides to Tof-SIMS mass spectrometric analysis of residual boron (boron-10 and boron-11). FIG. 12 shows that ~70% ethanol concentration is most effective in removing majority of the residual borate.

Figure 12A:
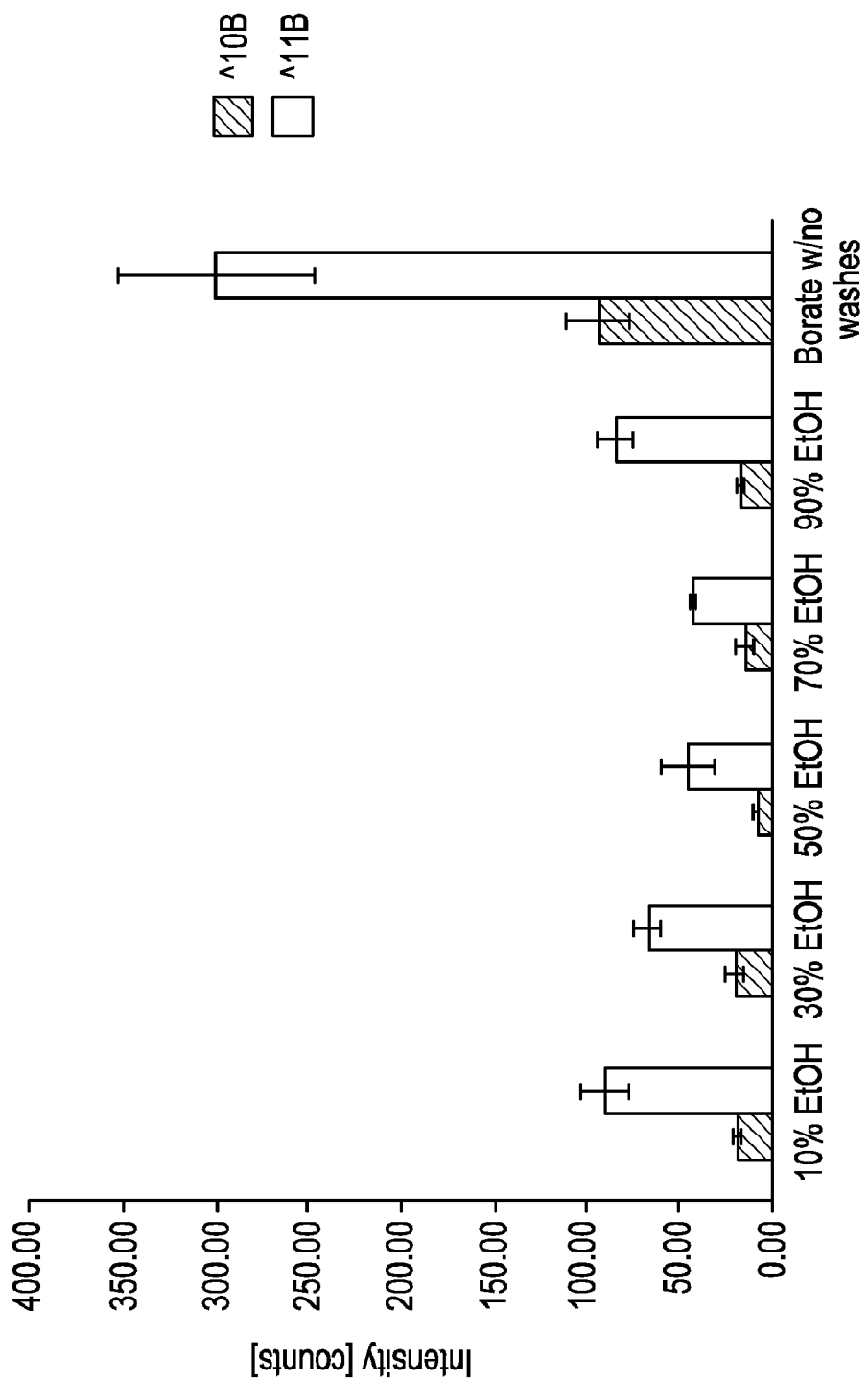
FIG. 12: Residual borate (as measured by boron content) after different washes in (a) lung squamous cell carcinoma tissue sample; (b) hapatocellular carcinoma tissue sample; (c) invasive ductal carcinoma of the breast tissue sample.

FIG. 12(a): Residual borate (as measured by boron content) after different washes in lung squamous cell carcinoma tissue sample.

Figure 12B:
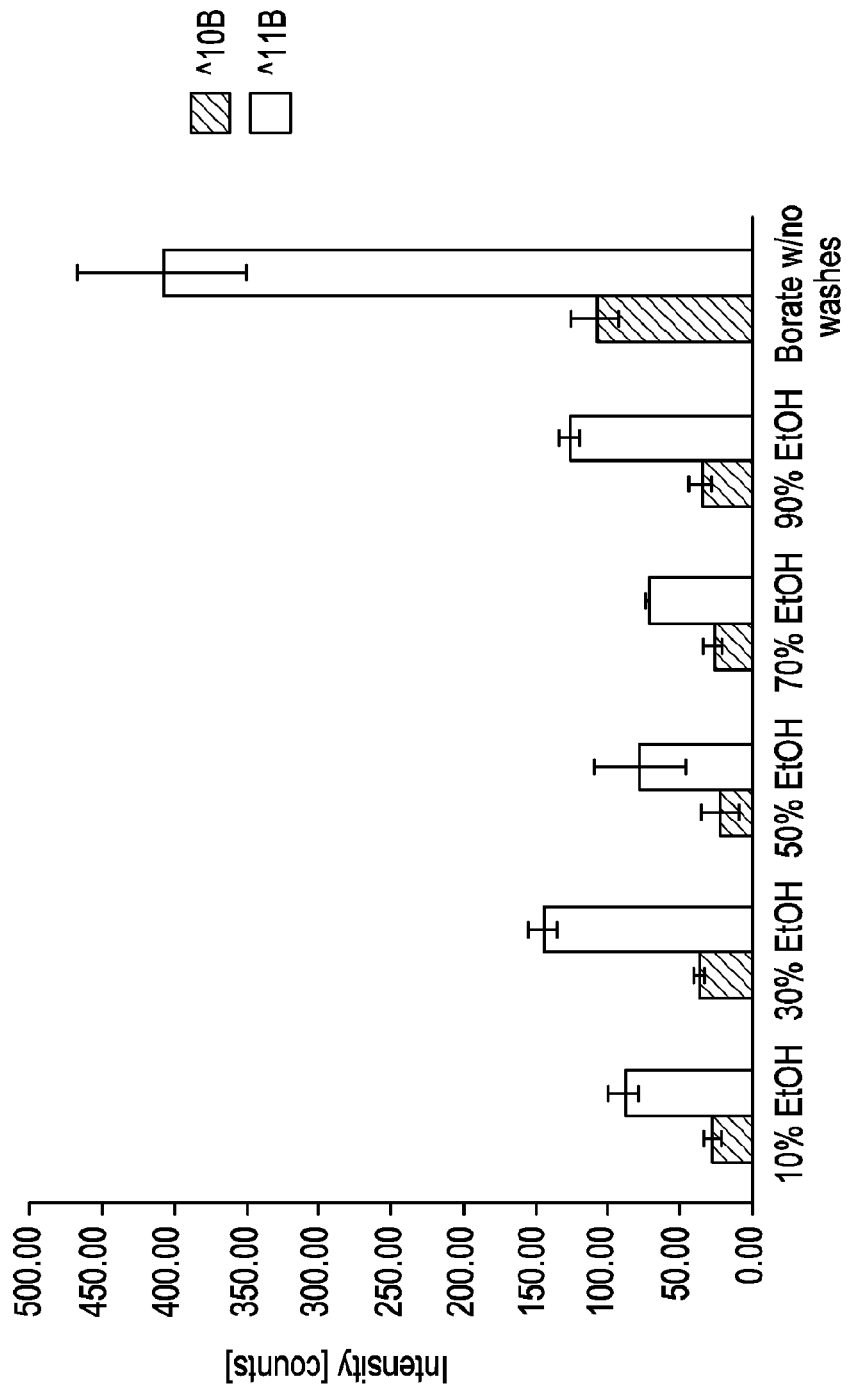

FIG. 12(b): Residual borate (as measured by boron content) after different washes in hapatocellular carcinoma tissue sample.

Figure 12C:
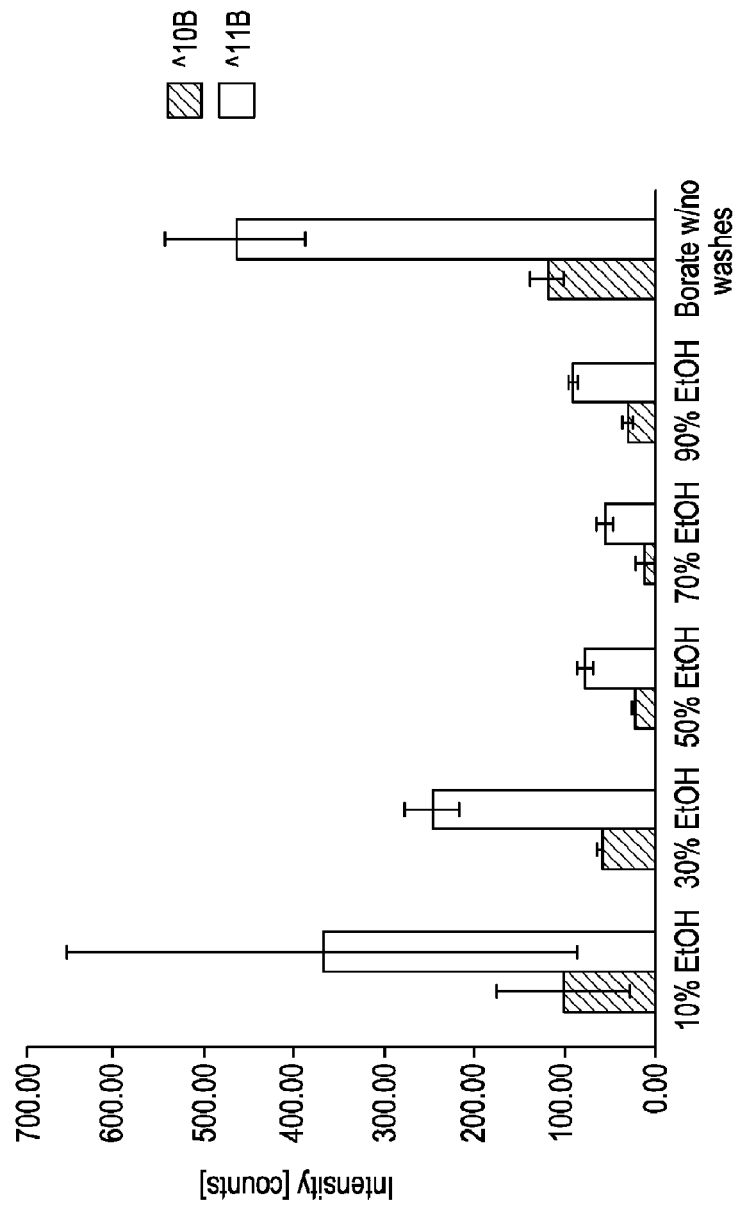

FIG. 12(c): Residual borate (as measured by boron content) after different washes in invasive ductal carcinoma of the breast. Similar results were observed with other tissue types tissue sample.

Example 9. Synthesis of Higher Water Solubility Borates (a) Preparation of diphenyl-bis-2-(4-(methoxyPEG (10)methyl)phenyl)ethyl borate-lithium Salt

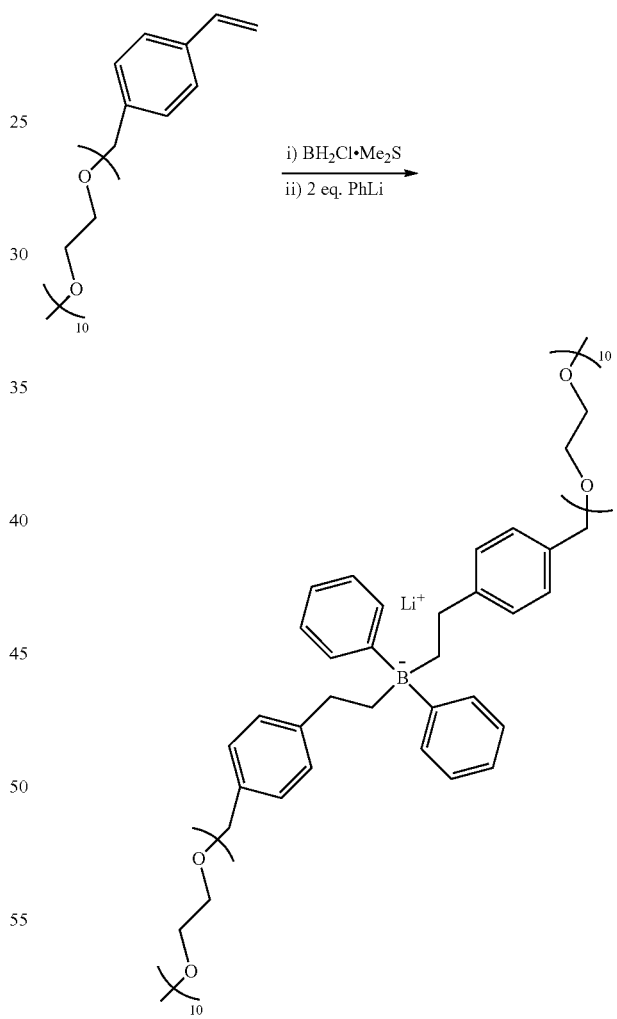

In a 250 mL 3-neck round bottom flask, equipped with a magnetic stir bar and nitrogen by-pass, was placed a solution of 10.0 g (13.7 mmole) 4-(methoxyPEG(10)methyl)-1-vinyl benzene in 80 mL of dry diethyl ether. The solution was cooled to 0° C. with an ice bath. Cloudy/opaque mixture was observed. To the solution was added dropwise through a syringe 00.714 ml (6.85 mmole) of chlorodihydorborane-dimethylsulfide complex. The opaque reaction solution was stirred at 0° C. for about 1 hour. The ice bath was removed and the reaction solution was analyzed by NMR indicating the presence of some starting material. It was then continued to stir at r.t. overnight. Analysis indicated that the reaction didn't go much further. The reaction solution was then cooled to 0° C. again and another 0.3 eq of the borane-complex was added. Ice bath was removed after 30 min and mixture stirred at r.t. for 3 hours.

The reaction mixture was cooled to −78° C. with dry ice-acetone bath. To the cooled mixture was added 7.4 mL (13.4 mmole) of phenyl lithium. Reaction mixture became viscous and partially solidified to a suspension (purple/brown solid). After 2 hours stirring at −78° C. the cooling bath was removed and mixture was allowed to warm up slowly to r.t. overnight with stirring. The solid became yellow in color. Ether was removed by decantation. The gummy solid was washed 2× with fresh diethyl ether with stirring. Solid was then dissolved in THF to wash with brine. THF layer was separated and concentrated to yield 2.5 g of crude product. The crude gummy solid was purified by dissolving in 800 ml of water (cloudy solution observed) and filtered. Water was then evaporated under reduced pressure and the residue, a cloudy light yellow liquid was dried under vacuum overnight. Yield: 1.79 g (16%)

$^1$H-NMR (D$_2$O); 7.22-7.66 ppm (d, m, 18H); 4.47 ppm (s, 4H), 3.73 ppm (t, 4H); 3.57 ppm (bs, 80H), 3.19 ppm, (s, 6H); 2.76 ppm (t, 4H).

(b) Preparation of phenyl-tris-2-(4-methoxyPEG(10)methylphenyl)ethyl borate-lithium Salt In a 100 mL 3-neck round bottom flask, equipped with a magnetic stir bar and nitrogen by-pass, was placed a solution of 3.82 g (5.22 mmole) 4-methoxyPEG(10)methyl)-1-vinyl benzene in 40 mL of dry diethyl ether. The solution was cooled to 0° C. with an ice bath. A slightly cloudy solution was observed. To the solution was added dropwise through a syringe, 0.14 ml (1.74 mmole) of chlorodihydroborane-dimethylsulfide complex. The reaction solution was stirred at 0° C. for about 15 min. The ice bath was removed and the reaction mixture was allowed to stir at r.t. for 4 hours until all the starting material disappeared (analyzed by $^1$H-NMR). The opaque reaction mixture was then cooled to −78° C. and 0.99 mL (1.74 mmole) of phenyl lithium was added dropwise through a syringe. The reaction mixture turned to a hot-pink color within 30 sec. It was stirred in the cooling bath overnight while slowly allowing it to warm up to room temp. After the evaporation of the solvent and the crude gummy solid was purified by dissolving in 500 mL water (cloudy solution observed) and filtered. Water was then evaporated under reduced pressure and the residue, a pale yellow liquid was dried under vacuum overnight.

$^1$HNMR (D$_2$O): 7.0-7.5 ppm (m, 19H); 4.54 ppm (s, 6H); 3.8 ppm (m, 6H); 3.63 ppm (bs, 120H), 3.37 (s, 9H), 2.8-3.0 ppm (m, 6H).

(c) Preparation of tetra-n-butylborate-lithium Salt

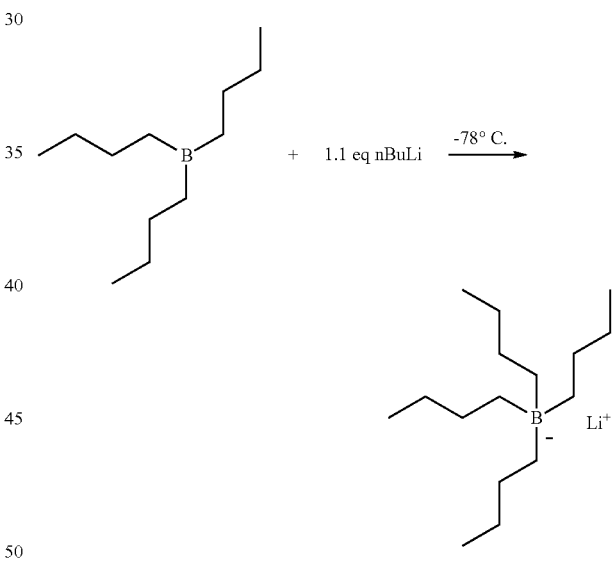

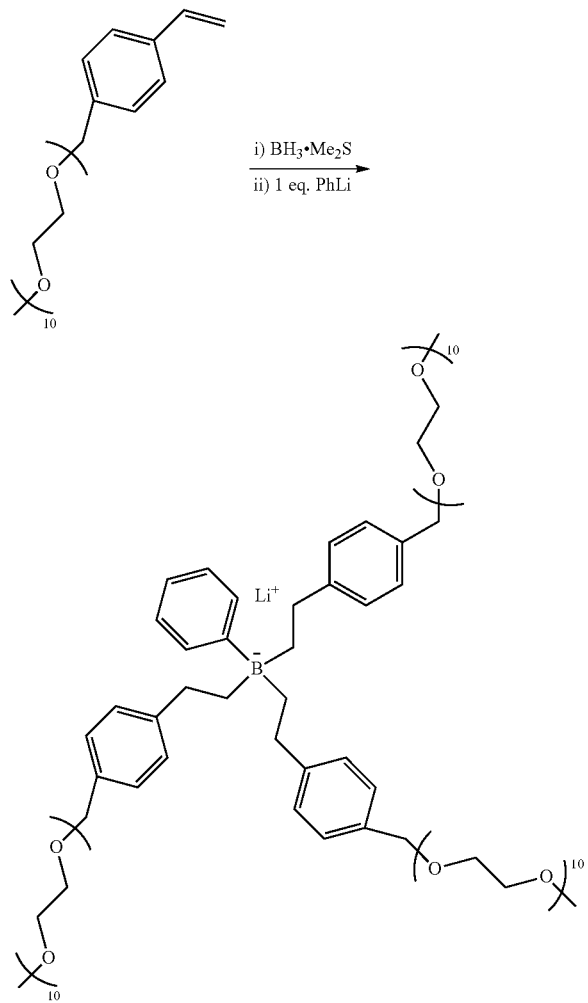

In a 250 3-neck round bottom flask was placed 20 mL (20 mmole) of 1.0M tri-n-butylborane in THF under nitrogen. Additional 40 mL of dried THF was added. The solution was cooled to −78° C. using a dry-ice acetone bath. To the cooled solution was added dropwise, through a syringe, 8.8 mL (22 mmole) 2.5M n-butyl lithium in hexane in about 10 min. After the addition was completed, the reaction solution was stirred at −78° C. for 1 hour and the cooling bath was removed to slowly warm up the reaction mixture to room temperature. It was then continued to stir overnight at room temperature under nitrogen.

The clear reaction solution was transferred to a round bottom flask in a dry nitrogen box and the solvent was then removed under reduced pressure. White solid was obtained. The solid was washed repeatedly with hexanes (3×100 mL) and dried. Yield: 5.7 g.

$^1$H-NMR (D$_2$O): 1.24 ppm (quintet, 8H), 1.08 ppm (quintet, 8H), 0.85 ppm (t, 12H), −0.14 ppm (m, 8H)

Figure 13:
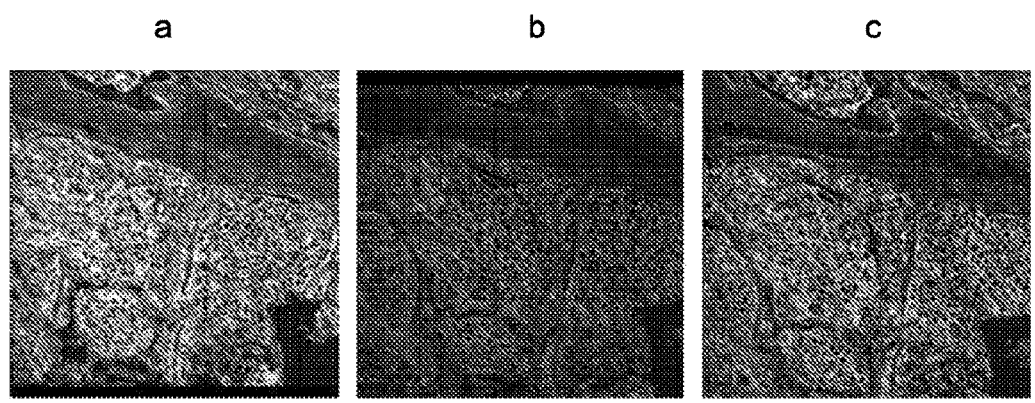
FIG. 13: Increased water solubility decreases borate retention as measured by its effect on signal from subsequent staining with anti-NaKATPase-Cy5 and light exposure. a) control slide treated with basic peroxide, b) slide bleached by PICB using monobenzyl triphenylborate, c) slide bleached with higher water solubility borate.

Example 10. Decreased Retention of High Water Solubility Borate as Measured by its Effect on Signal from Subsequent Staining Experiment was conducted as described above for Example 8. Experiment 1 except bleaching was performed with either monobenzyl triphenylborate as in Example 8, Experiment 1 or with a higher water solubility borate, a bis-(4-m-dPEG10-phenethyl)diphenylborate salt and after bleaching slides were only washed with PBS (3×5 min). FIG. 13 shows that most of the staining intensity is preserved (compared to control slide) after 1 min light exposure with the higher water solubility borate.

Example 11. Decreased Retention of High Water Solubility Borate as Measured by its Effect on Signal from Subsequent Staining Experiment was conducted as described above for Example 8, Experiment 1 except bleaching was performed with either monobenzyl triphenylborate as in Example 8, Experiment 1 or with a higher water solubility borate, tetrabutylborate salt and after bleaching slide treated with monobenzyl triphenylborate was washed with 70% ethanol (3×1 min) and then PBS (3×5 min) and slide treated with tetrabutylborate was washed with PBS (3×5 min) alone. FIG. 14 shows that tetrabutylborate doesn't require additional ethanol washes and is effectively removed by PBS alone giving a signal comparable to monobenzyl triphenylborate with 3 extra 70% ethanol washes.

Example 12. Automated Process for Photoactivated Chemical Bleaching

An automated device for iterative staining of a biological sample is described in US 20120135458. The automated device comprises a flow cell in fluid communication with a staining agent unit and a bleaching agent unit, wherein the flow cell comprises a surface configured to operatively engage the sample therewith, an illumination source for illuminating at least a portion of the biological sample, a monitoring unit operatively coupled to the flow cell and configured for monitoring one or moss optical characteristics of the biological sample before, during, and/or after the application of at least one of a staining agent and a bleaching agent. The device further comprises a processing unit for determining a figure of merit based on at least one of the optical characteristics of the biological sample, and a controller unit in communication with the processing unit and the flow cell, wherein the controller unit is configured to control the application of at least one of the staining agent and the bleaching agent based at least in part on the figure of merit. The term "figure of merit" includes, but is not limited to, a light intensity, a contrast of image, a Brenner gradient, or a signal to background ratio. A monitoring unit may comprise a microscope operatively coupled to a camera.

A closed loop automated method for staining a biological sample is also described in US 20120135458. The method comprises providing a biological sample in a flow cell, staining at least a portion of the biological sample, monitoring one or more optical characteristics of the biological sample during staining, and determining a figure of merit based on at least one of the optical characteristics. The method may further comprises rinsing at least a portion of the biological sample, monitoring one or more optical characteristics from the portion of the biological sample during rinsing, and determining a figure of merit based on at least one of the optical characteristics. The method may also comprise bleaching at least a portion of the biological sample, monitoring one or more optical characteristics from the portion of the biological sample during bleaching, and determining a figure of merit based on at least one of the optical characteristics. The biological sample may be incubated for a determined period of time after being stained to provide sufficient time for the antibodies to bind with the molecules in the biological sample. The imaging for the staining step may be performed during incubation period. In one example, monitoring during one or more of staining, bleaching and rinsing comprises acquiring images of the biological sample, and determining the figure of merit comprises determining a light intensity from the portion of the biological sample using the acquired images. Each of the staining, rinsing and bleaching steps may be accomplished by flowing a solution containing a particular reagent over the biological sample positioned within the flow cell. In some embodiments, the flow cell may be fixed on a microscope stage during the automated method.

Automation may be achieved through computer control of one or more of the process steps involved in staining cycle, such as but not limited to, addition of staining reagents and oxidant. Where the flow cell system is incorporated into a combined sample processing and image acquisition system, the image acquisition components (e.g., microscope or camera) may also be controlled by software such as a program written in LabVIEW or C.

Any suitable flow cell may be used for the automated method of staining of a biological sample. Representative flow cells am those disclosed in US20130287645 "Microfluidic chamber device and fabrication" and US20120135449 "Iterative staining of biological samples", both are herein incorporated by reference in its entirety.

An automated process for photoactivated chemical bleaching was performed according to the workflow of FIG. 15. This process began by the loading/capturing of a biological sample in a flow cell device. The flow cell chamber was then filled with at least one probe by flowing a solution containing the probe through the flow cell device. The probe was incubated under prescribed conditions and for a prescribed time in order for the probes to bind targets within the sample. Unbound, probes were rinsed out by flowing a wash buffer through the device. Images of the stained sample were captured. The flow cell chamber was next filled with an electron transfer reagent (monobenzyl triphenylborate (1 mM)) and an additive which prevents target modification during subsequent sample irradiation (DABCO (100 uM)). The sample was then irradiated by exposure to specific wavelengths of light, for one second, to inactivate signals from the probe (i.e., one second exposure with 10× objective Olympus IX-81 microscope). The electron transfer reagent and the additive were then rinsed out using a PBS buffer containing 70% ethanol. Images of the sample were captured to show the effectiveness of signal inactivation. Signal from the probe was no longer detectable (data not shown).

Before image capture, the flow cell chamber was optionally filled with a media that enhances image capture, by flowing the media through the device. After image capture, the media was rinsed out by flowing a wash buffer through the device.

After the electron transfer reagent and the additive are rinsed out, the flow cell chamber may be filled with at least one other probe, for another round of imaging and bleaching.

Sample irradiation may be accomplished by different methods. For example, sample irradiation may be accomplished by exposing specific regions of the sample with the desired wavelengths using optical filters and a microscope objective. An automated translation stage may allow for accurate positioning of the sample with respect to the objective. Multiple regions of the sample may be irradiated by moving the sample with respect to the objective between exposures. Alternatively, sample irradiation may be accomplished by exposing the entire sample at once with the desired wavelengths without focusing the light to a confined area.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A method of probing multiple targets in a biological sample comprising:
   (a) binding at least one probe to one or more targets present in the biological sample including multiple targets;
   (b) detecting a signal from the at least one probe bound in step (a);
   (c) contacting the sample comprising the bound probe of step (a) with an electron transfer reagent and an additive, wherein the additive is added in amount effective to prevent target modification in step (d) below;
   (d) irradiating the sample of step (c);
   (e) binding at least one probe to one or more targets present in the sample of step (d); and
   (f) detecting a signal from the probe bound in step (e).

2. The method of claim 1, wherein the probe in step (a) comprises an optical signal generator, and the signal detected in step (b) is an optical signal.

3. The method of claim 2, wherein the probe in step (a) comprises a fluorescent signal generator, and the signal detected in step (b) is a fluorescent signal.

4. The method of claim 3, wherein the electron transfer reagent is a high water solubility borate salt, having a water solubility of at least 20 mM.

5. The method of claim 1, wherein irradiating the sample in step (d) is carried out in the presence of a buffer at pH of 5-9.

6. The method of claim 1, wherein irradiating the sample in step (d) is accomplished by exposing the sample to light of 350 nm-1.3 μm in wavelength.

7. The method of claim 6, wherein irradiating the sample in step (d) is accomplished by exposing the sample to light of 400-700 nm in wavelength.

8. The method of claim 1, wherein the electron transfer reagent is a borate salt represented by the following structural formula:

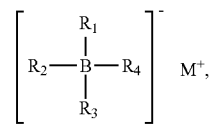

wherein:
   each $R_1$, $R_2$, and $R_3$ is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, and nitro,
   $R_4$ is an alkyl, an alkenyl, or an akynyl, wherein said alkyl, alkenyl, or alkynyl is optionally substituted with one or more substituents selected from the group consisting of (C1-C4)alkyl, (C1-C4)alkoxy, (C1-C4)alkylamino, amino, hydroxyl, cyano, halogen, and nitro, and
   $M^+$ is selected from the group consisting of organic and inorganic cations.

9. The method of claim 8, wherein each $R_1$, $R_2$, and $R_3$ is an optionally substituted aryl and $R_4$ is an optionally substituted alkyl.

10. The method of claim 9, wherein each $R_1$, $R_2$, and $R_3$ is unsubstituted phenyl and $R_4$ is unsubstituted butyl, and the borate salt is triphenylbutyl borate salt.

11. The method of claim 1, wherein said probe bound in step (a) and/or step (b) is a morphological stain.

12. The method of claim 1, wherein steps (c)-(f) are repeated one or more times.

13. The method of claim 1, wherein the steps (c) and (d) are performed for about 100 milliseconds to about 15 minutes.

14. The method of claim 1, further comprising, after step (d), washing the sample with a wash solution that effectively removes residual electron transfer reagents from the sample.

15. The method of claim 14, wherein said wash solution contains an enabler.

16. The method of claim 1, wherein the probe in step (a) and the probe in step (e) each comprise a signal generator, wherein the signal generator in step (a) is different from the signal generator in step (e).

17. The method of claim 1, wherein irradiation of sample in step (d) initiates a photoreaction that substantially inactivates a signal generator in the probe bound in step (a) by photoactivated chemical bleaching.

18. The method of claim 1, wherein no detectable signal is detected after step d).

19. The method according to claim 1, wherein binder and signal generator are embodied in a single entity.

20. The method according to claim 19, wherein the single entity is a small molecule probe.

21. The method according to claim 20, wherein the small molecule probe is an organic dye.

22. The method according to claim 21, wherein the organic dye binds specific structures or proteins in the sample.

23. A method of probing multiple targets in a biological sample comprising:
   (a) binding at least one probe to one or more targets present in the biological sample including multiple targets;

(b) detecting a signal from the at least one probe bound in step (a);
(c) contacting the sample comprising the bound probe of step (a) with an electron transfer reagent and an additive which prevents target modification in step (d) below, wherein the additive is a quencher for singlet oxygen;
(d) irradiating the sample of step (c);
(e) binding at least one probe to one or more targets present in the sample of step (d); and
(f) detecting a signal from the probe bound in step (e).

24. The method of claim 23, wherein the quencher for singlet oxygen is selected from the group consisting of ascorbic acid, a-tocopherol, curcurmin and DABCO.

25. The method of claim 23, wherein the probe in step (a) comprises an optical signal generator, and the signal detected in step (b) is an optical signal.

26. The method of claim 25, wherein the probe in step (a) comprises a fluorescent signal generator, and the signal detected in step (b) is a fluorescent signal.

27. The method of claim 26, wherein the electron transfer reagent is a high water solubility borate salt, having a water solubility of at least 20 mM.

28. The method of claim 23, wherein irradiating the sample in step (d) is carried out in the presence of a buffer at pH of 5-9.

29. The method of claim 23, wherein irradiating the sample in step (d) is accomplished by exposing the sample to light of 350 nm-1.3 µm in wavelength.

30. The method of claim 29, wherein irradiating the sample in step (d) is accomplished by exposing the sample to light of 400-700 nm in wavelength.

31. The method of claim 23, wherein the electron transfer reagent is a borate salt represented by the following structural formula:

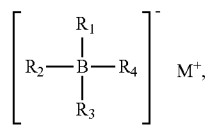

wherein:
each $R_1$, $R_2$, and $R_3$ is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, and nitro,
$R_4$ is an alkyl, an alkenyl, or an akynyl, wherein said alkyl, alkenyl, or alkynyl is optionally substituted with one or more substituents selected from the group consisting of (C1-C4)alkyl, (C1-C4)alkoxy, (C1-C4)alkylamino, amino, hydroxyl, cyano, halogen, and nitro, and
$M^+$ is selected from the group consisting of organic and inorganic cations.

32. The method of claim 31, wherein each $R_1$, $R_2$, and $R_3$ is an optionally substituted aryl and $R_4$ is an optionally substituted alkyl.

33. The method of claim 32, wherein each $R_1$, $R_2$, and $R_3$ is unsubstituted phenyl and $R_4$ is unsubstituted butyl, and the borate salt is triphenylbutyl borate salt.

34. The method of claim 23, wherein said probe bound in step (a) and/or step (b) is a morphological stain.

35. The method of claim 23, wherein steps (c)-(f) are repeated one or more times.

36. The method of claim 23, wherein the steps (c) and (d) are performed for about 100 milliseconds to about 15 minutes.

37. The method of claim 23, further comprising, after step (d), washing the sample with a wash solution that effectively removes residual electron transfer reagents from the sample.

38. The method of claim 37, wherein said wash solution contains an enabler.

39. The method of claim 23, wherein the probe in step (a) and the probe in step (e) each comprise a signal generator, wherein the signal generator in step (a) is different from the signal generator in step (e).

40. The method of claim 23, wherein irradiation of sample in step (d) initiates a photoreaction that substantially inactivates a signal generator in the probe bound in step (a) by photoactivated chemical bleaching.

41. The method of claim 23, wherein no detectable signal is detected after step d).

* * * * *